(12) United States Patent
Kurihara et al.

(10) Patent No.: US 9,193,963 B2
(45) Date of Patent: Nov. 24, 2015

(54) MUTANT ENDOGLUCANASE

(71) Applicants: Toray Industries, Inc., Tokyo (JP); National Institute of Advanced Industrial Science and Technology, Tokyo (JP)

(72) Inventors: Hiroyuki Kurihara, Kamakura (JP); Takeshi Tsukada, Kamakura (JP); Katsushige Yamada, Kamakura (JP); Yumiko Mishima, Higashihiroshima (JP); Yuka Maeno, Higashihiroshima (JP); Kazuhiko Ishikawa, Higashihiroshima (JP)

(73) Assignees: Toray Industries, Inc. (JP); National Institute of Advanced Industrial Science and Technology (JP)

( * ) Notice: Subject to any disclaimer, the term of this patent is extended or adjusted under 35 U.S.C. 154(b) by 0 days.

(21) Appl. No.: 14/195,923

(22) Filed: Mar. 4, 2014

(65) Prior Publication Data

US 2014/0178947 A1    Jun. 26, 2014

Related U.S. Application Data

(63) Continuation of application No. PCT/JP2012/072401, filed on Sep. 4, 2012.

(30) Foreign Application Priority Data

Sep. 5, 2011   (JP) .................................. 2011-193279

(51) Int. Cl.
    *C12N 9/42* (2006.01)
    *C12P 19/02* (2006.01)
    *C13K 1/02* (2006.01)
    *C12P 19/14* (2006.01)

(52) U.S. Cl.
    CPC ............. *C12N 9/2437* (2013.01); *C12P 19/02* (2013.01); *C12P 19/14* (2013.01); *C13K 1/02* (2013.01)

(58) Field of Classification Search
None
See application file for complete search history.

(56) References Cited

FOREIGN PATENT DOCUMENTS

WO   2010/096931   9/2010
WO   2013/035678 A1   3/2013

OTHER PUBLICATIONS

Corresponding Supplementary European Search Report dated Feb. 20, 2015 of European Application No. 12830699.0.
Database UniProt [Online], "SubName: Full:Putative uncharacterized protein {ECO:0000313|EMBL:EGG15019.1 }," XP002735633, Jun. 28, 2011.
R.M. Vohra et al., "Effect of Lignin and Some of its Components on the Production and Activity of Cellulase(s) by Trichoderma reesei," Biotechnology and Bioengineering, vol. XXII, 1980, pp. 1497-1500.
S.S. Paul et al., "Effect of phenolic monomers on biomass and hydrolytic enzyme activities of an anaerobic fungus isolated from wild nil gai (*Baselophus tragocamelus*)," Letters in Applied Microbiology, vol. 36, 2003, pp. 377-381.
Yasuhiro Kashima et al., "Analysis of the function of a hyperthermophilic endoglucanase from *Pryococcus horikoshii* that hydrolyzes crystalline cellulose," Extremophiles, vol. 9, Issue 1, Feb. 2005, pp. 37-43 (Abstract only).
Han-Woo Kim et al., "Analysis of the Putative Substrate Binding Region of Hyperthermophilic Endoglucanase from *Pyrococcus horikoshii*," Biosci. Biotechnol. Biochem., vol. 71, No. 10, 2007, pp. 2585-2587.
Kang Hee-Jin et al., "Analysis of Active Center in Hyperthermophilic Cellulase from *Pyrococcus horikoshii*," J. Microbiol. Biotechnol., vol. 17, No. 8, 2007, pp. 1249-1253.
Eduardo Ximenes et al., "Inhibition of cellulases by phenols," Enzyme and Microbial Technology, vol. 46, 2010, pp. 170-176.
Han-Woo Kim et al., "Structure of hyperthermophilic endocellulase from *Pyrococcus horihoshii*," Proteins, vol. 78, Issue 2, Feb. 1, 2010, pp. 496-500.
Han-Woo Kim et al., "Functional analysis of hyperthermophilic endocellulase from *Pyrococcus horikoshii* by crystallographic snapshots," Biochem J., vol. 437, 2011, pp. 223-230.

*Primary Examiner* — Suzanne M Noakes
(74) *Attorney, Agent, or Firm* — DLA Piper LLP (US)

(57) ABSTRACT

Endoglucanase characterized by a decreased degree of activity inhibition by a lignin-derived aromatic compound, and prepared by substituting tryptophan at position 273 in the amino acid sequence of wild-type thermophilic bacterium-derived endoglucanase with an amino acid other than aromatic amino acids.

15 Claims, 4 Drawing Sheets

Fig. 1-1

```
EGPh    MEGNTILKIVLICTILAGLFGQVVPVYAENTTYQTPTGIY-YEVRGDTIYMINVTSG---
EGIa2   ------------------------------------------MYREKSCGSTIMDVY--YRARGTEIYIE--RKG---
EGIa1   ------------------------------------------------------------MN-FFVKNGEIYKLDGATG---
EGSh    ----MPARTRIACAVI--LLLVFLALYIAWPVEGSFLKQQPYNELRGRVLGSNIQIPKDH
EGPa    -------MEIKLFC-------VFIVFIILFSPFVIALSYPDVN-YTAENGIIFVQNVTTG---
EGSt    ---------MKYLRTILLSLLVFLITLGCSLPFLDVS--GKGGTAARATELRVG---
EGAc    ----MPRALRRVPGSRVMLRVGVVVAVLAVAALANLAVPRPARAAGGGYWHTSGRE---
                                                            :

EGPh    -------------EETPIHLFGVNWFGFETPNHVVHGLWKRNWEDMLLQIKSLGFNAIRL
EGIa2   -------------VEKPLYIFGINWAGFEWRGRVVGGLHVRNWVEILQQIKSLGFNAIRI
EGIa1   -------------KPKIIYLFGVNWFGFETRDYVVHGLWARNWVDMLQQIKSLGFNAIRL
EGSh    IPYYHIVNGTIYMDDKLIHLFGVSWFGFELPDHIVYGLWARNWKDILKDIKEMGFNAIRL
EGPa    -------------EKKPLYLHGVSWFGFELKDHVVYGLDKRNWKDILKDVKRLGFNAIRL
EGSt    -------------RLTGVNWFGFETGNHVVHGLWARDYKSMLKQIADLGFNCIRI
EGAc    -------------ILDANNVPVRIAGINWFGFETCNYVVHGLWSRDYRSMLDQIKSLGYNTIRL
                          :  *.*  ** **   :  * **  **:. .:.  .:*:.**:

EGPh    PFCTESVKPGTQPIG-------IDYSKNPDLRGLDSLQIMEKIIKKAGDLGIFVLLD
EGIa2   PFCAESVKPGVFPAPR------TINYALNRDLIGLDSISIMEKIIAKAAELELYILLC
EGIa1   PFCTYSVQEGTMPNSN------AINYNINPDLQGLTSIEIMEKIVAKANELGIYILLD
EGSh    PFCHESITPGTKPVPG------RISYSLNPDLRNLTSLEIMEKIISYANELNIFVLLD
EGPa    PFCSESIRPDTRPSPE------RINYELNPDLKNLTSLEIMEKIIEYANSIGLYILLD
EGSt    PWANEMIDKAPNSIQINPSGVDPYTGEQGLNLDLEGLSSLEVLDKIIEEANRIGLYVILD
EGAc    PYSDDILKPGTMPNSIN-----FYQMNQDLQGLTSLQVMDKIVAYAGQIGLRIILD
        *  :                  . ** .* .*:::::**: *      ::  ::*
```

Fig. 1-2

```
EGPh   YHRIGCT--HIEPLWYTEDFSEEDFINTWIEVAKRFGKYWNVIGADLKNEPHSVTSPPAA
EGIa2  FHNISCL--IMEPLWYTPLFSEQFIDTWIRVAKRFSRYWNVIGAELYNNPHGRLPPSYY
EGIa1  YHRLGCD--QIEPLWYSDQVSEQQFIDTWVSVAKRFAKYPNVIGADIRNEPWG-------
EGSh   YHRIGCR--YIEPLWYTDNFSEEQYIKDWVFLAQKFGKYPNVIGADIKNEPHD-------
EGPa   YHRIGCE--EIEPLWYTENYSEEQYIKDWIFLAKRFGKYPNVIGADIKNEPHG-------
EGSt   NHSRAADGYMNETLWYTDEYPEERWISDWVMVRRYKNYPNVIGADLNNEPHGNTGTG---
EGAc   RHRPDCS--GQSALWYTSSVSEATWISDLQALAQRYKGNPTVVGFDLHNEPHD-------
         *        . **.       ..:. .    *:.        .  *:*. ** .*:*.

EGPh   YTDGTGATWGMGNPAT---DWNLAAERIGKAILKVAPHWLIFVEGTQFTNPKTDS---SY
EGIa2  YESGECATWGMGNPKT---DWNLAAERIGRAVLEVAPHWLIIVKGTQLTNPRSDN---VP
EGIa1  ----ATWGTDDPAT---DWRLAVEKVAPKILEVAPHWLIFVEGTYKTRPDIDERSWYP
EGSh   SASWGTGDNKT---DFRLFAERVGQAILQVAPHWLIFIEGVQYTHVP----EIDG
EGPa   ----EAGWGTGDER-----DFRLFAEKVGREILKVAPHWLIFVEGTQYTHVPNID-EIIE
EGSt   --MKPPATWGYTLPEYGDTDWKAAAERCAAAILAENPNLYIIVEGVEEYQGDT-------
EGAc   ----PACWGCGDPSI----DWRLAAERAGNAVLSVNPNLLIFVEGVQSYNGDS-------
            .  *        .  *:.  *     .* ...*   *  ..:

EGPh   KWGYNAWWGGNLMAVKDYPVN-LPRNKLVYSPHVYGPDVYNQPYFGPAKGFPDNLPDIWY
EGIa2  LYPEATYWGENLRAVRDYPVN-LPRDKLVYGVDIYGPDVYMPYFNDPNIFPDKLYLIWD
EGIa1  YYSYYVFWGENLRAVRYYPVR-LPYEKIVYSPHTYGPDVFRQPYFDDP-IFPENMRSIWM
EGSh   RNPYSCFWGENLMGVKDYPVR-LPKDKIVYSPHVYGPSVYNMPYFNDP-EFPRNLPKIWE
EGPa   KKGWWTFWGENLMGVKDYPVR-LPRGKVVYSPHVYGPSVYMMDYFKSP-DFPNNMPIIWE
EGSt   ----YWWGGNLKGVRDYPITSIPAENLIYSPHEYGPEVYNQSWFSDP-TFPDNMPAIWD
EGAc   ----YWWGGNLQGAGQYPVVLNVPNRLVYSAHDYATSVYPQTWFSDP-TFPNNMPGIWN
           :* **  .. ..** .  : **:. * . *    :..  . .   **
```

Fig. 1-3

```
EGPh    HHFGYVKLELGYSVVIGEFGGKYGHGGDPRDVIWQNKLVDWMIENKFC------DFFYWSW
EGIa2   QNWGYVKKELGYPLIIAEFGGLYGRG-DPRDVIWHQKLVEYMISNNIC------HWFYNAL
EGIa1   ERFGYVKTELGYALVVGEFGGRYGHGGDPRDIIWQIKFVDWLIENRIC------NFFYWSW
EGSh    LHFGYLK-ELGYAIVIGEWGGRYVGK-----DKVWQDAFADWLIQKGIY------DFFYWCL
EGPa    THFGYLT-DLNYTLVIGEWGGNYEGL-----DKVWQDAFVKWLIKKKIY------NFFYWCL
EGSt    EHFWFIYKENIAPVLIGEFGIKEASAADPSSVAYQWFTFMAYVGDKA-------SWTFWSW
EGAc    KNWGYLFNQNIAPVWLGEFGTTLQST---TDQTWLKTLVQYLRPTAQYGADSFQWTFWSW
         *:.    .  . :: .**  .           .                     .  ::.*

EGPh    NPDSGDTGGILQDDWTTIWEDKYNNLKRLMDSCS---------KSSSSTQS-------
EGIa2   NPDNPSTAGLLENDWRTVREDKMALLRRAMDYCR---------ERYGNI---------
EGIa1   NANSGDTGGILKDDWTNIWEDKYQNLKRLMDYCS---------SIN-----------
EGSh    NPESGDTGGIFKSDWRTVNQDKLNLIHRIINAAS---------QAQAST---------
EGPa    NPESGDTGGIFLDDWKTVNWEKMRVIYRLIKAANPEFEEPLYIILKTNATTSILGVGERI
EGSt    NPNSGDTGGILKDDWVTVNEAKYNLIRPYLANPPQP-------TATPTPGTPTPTPTP
EGAc    NPDSGDTGGILKDDWQTVDTVKDGYLAPIKSSIFDPVG--ASASPSSQPSPSVSPSPSP
         *.: .*..*:::  .**   .                     :

EGPh    --------------------------------------------------------
EGIa2   --------------------------------------------------------
EGIa1   --------------------------------------------------------
EGSh    -----------ISG-----------------------------------------
EGPa    RIYWYTNGKVIDSNFAHSSEGEMNITVTKSMTLYIIVKKGNQTLRKELKLYVIGGNYGSN
EGSt    TPTPTPTPTPTPTPTPTPTPTPTATPTPTPTPTATPTPSGEYTEIALPFSYDGAGEYY
EGAc    SPSASRTPTPTPTPTASPTPTLTPTATPTPTASPTTPSPTAASGARCTASYQVNSDWGNGF
```

Fig. 1-4

```
EGPh    ------------------VIRSTTPTKSNTSKKKICGPAILIILAVFSLLLRRAPR------------------
EGIa2   ---------------------------------------------------------------------------
EGIa1   ---------------------------------------------------------------------------
EGSh    --------LIAP--------TLLPVLILVLLIKRRYTKKQ-----------------------------------
EGPa    ISTTQLVTPKKGGERISTSLKLAISLLFILLFVWYLLREKH----------------------------------
EGSt    WKTDQFSTDPNDWSRYVNSWNLDLLEINGTDYTNVWVAQHQIPAASDGYWYIHYKSGVSW
EGAc    TVTVAVTNSGSVATKTWTVSWTFGGNQTITNSWNAAVTQNGQSVTARNMSYNNVIQPGQN

EGPh    ---------------
EGIa2   ---------------
EGIa1   ---------------
EGSh    ---------------
EGPa    ---------------
EGSt    GHVEIK---------
EGAc    TTFGFQASYTGSNAAPTVACAAS
```

MUTANT ENDOGLUCANASE

TECHNICAL FIELD

This disclosure relates to a novel mutant endoglucanase.

BACKGROUND

In recent years, the production of ethanol or raw materials for chemical products from cellulose, which is a regenerable and carbon neutral resource, has been in strong demand in response to problems such as fossil resource depletion and global warming.

Cellulose is contained in abundance in herbaceous plants and woody plants, which are collectively referred to as cellulosic biomass. The cell walls of cellulosic biomass are mainly composed of cellulose, hemicellulose, and lignin. Cellulose is a linear polysaccharide comprising glucose molecules joined by β-1,4 linkages. Hemicellulose is a polysaccharide such as xyloglucan, xylan, or mannan. Lignin is an aromatic macromolecular compound with a complicated structure, intertwined with cellulose and hemicellulose within cell walls to form a three-dimensional mesh structure.

The production of ethanol or raw materials for chemical products from cellulosic biomass requires a step referred to as "saccharification" by which cellulosic biomass is degraded into monosaccharides that can be fermented by microorganisms. Examples of typical saccharification processes include acid treatment and enzyme treatment. Acid treatment involves a large amount of waste water, imposing a great environmental burden. Hence, enzyme treatment, which involves performing a reaction under moderate conditions using cellulase, is currently the mainstream treatment under development.

Cellulase is a generic name applied to cellulose-hydrolyzing enzymes, which are classified into three types based on substrate specificity differences: cellobiohydrolase, endoglucanase, and β-glucosidase. They are believed to act in concert so that cellulose is hydrolyzed.

When cellulosic biomass is saccharified using cellulase, the activity of cellulase is inhibited by various factors such as substrate inhibition, product inhibition, and non-specific adsorption. Furthermore, it is known that the activity of cellulases such as endoglucanase is inhibited by lignin-derived aromatic compounds (R. M. Vohra et al., Biotechnol. Bioeng., 22, 1497-1500 (1980), S. S. Paul et al., Lett. Appl. Microbiol., 36, 377-381 (2003) and E. Ximense et al., Enzym Microb Tech., 46, 170-176 (2010)). However, the mechanisms of inhibition remain unknown.

The enzymes produced by thermophilic bacteria or hyperthermophilic bacteria are highly stable and thus can retain their activity even under high-temperature conditions for long periods of time. Hence, the application thereof as industrial enzymes has been examined. Cellulases produced by cellulose-degrading thermophilic bacteria or hyperthermophilic bacteria have also been studied. It has been revealed that most of the cellulase genes of these bacteria encode endoglucanases.

SUMMARY

It is known that when cellulosic biomass is saccharified using cellulases, the activity of cellulases such as endoglucanase is inhibited by a lignin-derived aromatic compound. We provide mutant endoglucanase characterized by a significantly decreased degree of activity inhibition by a lignin-derived aromatic compound. Furthermore, we provide a method of producing a sugar solution by hydrolyzing cellulose, and in particular, cellulosic biomass containing lignin, wherein an enzyme composition with high degradation efficiency is used.

We succeeded in obtaining a mutant endoglucanase having properties such as improved functions by introducing an amino acid mutation to a specific position in a thermophilic bacterium-derived endoglucanase. Specifically, we focused on the three-dimensional structure of the wild-type parent endoglucanase, identified amino acids associated with the formation of a complex structure of the parent endoglucanase and a lignin-derived aromatic compound using protein crystal structure analysis, selectively added mutations to the amino acids, and thus succeeded in obtaining an endoglucanase characterized by a significantly decreased degree of activity inhibition by the lignin-derived aromatic compound.

We thus provide the following [1] to [12]:

[1] A mutant endoglucanase, comprising an amino acid sequence wherein, in the amino acid sequence of a thermophilic bacterium-derived endoglucanase, an amino acid residue corresponding to the 273rd tryptophan in the amino acid sequence of SEQ ID NO: 1 is substituted with an amino acid selected from amino acids other than aromatic amino acids.

[2] The mutant endoglucanase of [1], wherein the amino acid sequence of the thermophilic bacterium-derived endoglucanase comprises any one of the following amino acid sequences:
  (a) the amino acid sequence shown in SEQ ID NO: 1, 7, 13, 19, 25, 31, or 37, which encodes a protein having endoglucanase activity;
  (b) an amino acid sequence that has a deletion, a substitution, or an addition of 1 to several amino acids with respect to the amino acid sequence shown in SEQ ID NO: 1, 7, 13, 19, 25, 31, or 37 and encodes a protein having endoglucanase activity; and
  (c) an amino acid sequence that has 90% or more sequence identity with the amino acid sequence shown in SEQ ID NO: 1, 7, 13, 19, 25, 31, or 37 and encodes a protein having endoglucanase activity.

[3] The mutant endoglucanase of [1] or [2], wherein the amino acid residue corresponding to the 273rd tryptophan in the amino acid sequence of SEQ ID NO: 1 is substituted with alanine

[4] The mutant endoglucanase of any one of [1] to [3], comprising the amino acid sequence shown in SEQ ID NO: 2, 8, 14, 20, 26, 32, or 38.

[5] DNA encoding the mutant endoglucanase of any one of [1] to [4].

[6] DNA of [5], comprising the nucleotide sequence shown in SEQ ID NO: 4, 10, 16, 22, 28, 34, or 40.

[7] An expression vector, comprising the DNA of [5] or [6].

[8] Transformed cells, which are prepared by transformation using the expression vector of [7].

[9] A method for producing a mutant endoglucanase, comprising the steps of:
  (1) culturing the transformed cells of [8]; and
  (2) purifying the mutant endoglucanase produced by the transformed cells.

[10] A composition for degrading biomass, containing the mutant endoglucanase of any one of [1] to [4] and/or a treated product of the transformed cells of [8].

[11] A method for producing a sugar solution from cellulose-derived biomass, comprising adding the composition for degrading biomass of [10] to a cellulose-containing biomass suspension and then hydrolyzing the cellulose-containing biomass.

[12] The method of [11], further comprising adding filamentous bacterium-derived cellulase.

Our mutant endoglucanase is characterized by a significantly decreased degree of activity inhibition by a lignin-derived aromatic compound. Accordingly, lignocellulose can be degraded with high efficiency when a sugar solution is produced by hydrolysis of cellulose, and in particular, cellulosic biomass containing lignin. Therefore, a sugar solution can be efficiently produced using the mutant endoglucanase as an enzyme composition.

BRIEF DESCRIPTION OF THE DRAWINGS

FIG. 1-1 shows alignment of the sequence of the *Pyrococcus horikoshii*-derived endoglucanase (EGPh) (SEQ ID NO: 1) and that of the thermophilic bacterium-derived endoglucanase of Example 1. Tryptophan at position 273 in SEQ ID NO: 1 is underlined. EGPh: SEQ ID NO: 1; EGIa2: SEQ ID NO: 13; EGIa1: SEQ ID NO: 7; EGSh: SEQ ID NO: 19; EGPa: SEQ ID NO: 25; EGSt: SEQ ID NO: 37; EGAc: SEQ ID NO: 31.

FIG. 1-2 is a continuation from FIG. 1-1.
FIG. 1-3 is a continuation from FIG. 1-2.
FIG. 1-4 is a continuation from FIG. 1-3.

DETAILED DESCRIPTION

We provide a mutant endoglucanase characterized by a significantly decreased degree of activity inhibition by a lignin-derived aromatic compound, compared with that of the parent endoglucanase.

The term "lignin-derived aromatic compound" as used herein is not particularly limited as long as it is an aromatic compound that is a lignin precursor generally referred to as a monolignol, an aromatic compound present in the biosynthetic pathway thereof, or an aromatic compound obtained by degrading cellulosic biomass. Alternatively, a lignin-derived aromatic compound as used herein may also be a mixture of one or more types thereof. Examples of an aromatic compound referred to as monolignol and an aromatic compound present in the biosynthetic pathway thereof include coniferyl alcohol, sinapyl alcohol, p-coumaryl alcohol, phenyl alanine, cinnamic acid, p-coumaric acid, caffeic acid, 5-hydroxyferulic acid, synapoic acid, p-coumaroyl coenzyme A, caffeoyl coenzyme A, feruloyl coenzyme A, 5-hydroxy feruloyl coenzyme A, sinapoyl coenzyme A, p-coumaryl aldehyde, caffeyl aldehyde, 5-hydroxyconiferyl aldehyde, sinapyl aldehyde, caffeyl alcohol, 5-hydroxyconiferylalcohol, 5-dehydroshikimic acid, shikimic acid, shikimate-5-phosphate, 3-enolpyruvylshikimate-5-phosphate, chorismic acid, prephenic acid, phenyl pyruvic acid, p-hydroxyphenyl pyruvic acid, tyrosine, and sinap aldehyde. Examples of those obtained by degradation of cellulosic biomass include syringa aldehyde, p-hydroxybenzaldehyde, 5-formylvanillin, vanillic acid, syringic acid, 5-formylvanillic acid, 5-carboxy vanillin, acetoguaiacon, guaiacol, vanillyl alcohol, dihydroconiferyl alcohol, syringaldehyde, 5-hydroxylmethylvanillin, 1-guaiacyl-1-buten-3-one, p-methoxyazobenzene, benzoic acid, p-hydroxybenzoic acid, o-phthalic acid, terephthalic acid, isophthalic acid, trimethylgallic acid, vanilloyl formic acid, hemimellitic acid, trimellitic acid, isohemipinic acid, trimesitinic acid, prehnitic acid, pyromellitic acid, mellophanic acid, benzene pentacarboxylic acid, benzene hexacarboxylic acid, dehydrodivanillic acid, 4,4'-dihydroxy-3,3'-dimethoxy chalkone, 4,4'-dihydroxy-3,3'-dimethoxy-benzil, diguaiacyl glycolic acid, 4,4'-dihydroxy-3,3'-dimethoxybenzophenone, diformyl dihydroxy-dimethoxy-diethyl stilbene, veratric acid, isohemipinic acid, metahemipinic acid, hemipinic acid, benzene polycarboxylic acid, sinapinic acid, furfural, hydroxymethylfurfural, ferulamide, and coumaramide. Preferable examples thereof include ferulic acid, vanillin, and coniferyl aldehyde.

The term "endoglucanase" as used herein is an enzyme that hydrolyzes β-1,4-glycosyl linkages of cellulose or the like to generate glucose, cellobiose, and cellooligosaccharide, for example. An enzyme group belonging to endoglucanase is described under EC No.: EC3.2.1.4. Examples of "endoglucanase" include proteins that do not belong to endoglucanase under EC No., but have the above endoglucanase activity. Specific examples thereof include xylanase, xyloglucanase, mannanase, chitinase, chitosanase, and galactanase.

The term "parent endoglucanase" as used herein refers to an endoglucanase having an amino acid sequence before introduction of a mutation, which exhibits the above-mentioned endoglucanase activity. The term "parent endoglucanase" as used herein may also be referred to as "wild-type." In this case, the terms "parent endoglucanase" and "wild-type" are used interchangeably. "Parent endoglucanase" is preferably derived from a thermophilic bacterium.

The term "thermophilic bacterium (bacteria)" as used herein is a generic name of a group of microorganisms capable of growing at 50° C. or higher. Particularly the term "hyperthermophilic bacterium (bacteria)" refers to a group of microorganisms capable of growing at 80° C. or higher. Examples of the thermophilic bacteria include the genus *Pyrococcus*, the genus *Ignisphaera*, the genus *Staphylothermus*, the genus *Acidthermus*, the genus *Spirochaeta*, the genus *Sulfolobus*, the genus *Thermoplasma*, the genus *Caldivirga*, the genus *Thermosphaera*, the genus *Picrophilus*, and the genus *Fervidobacterium*.

A thermophilic bacterium-derived endoglucanase is known and registered at the GenBank under AAQ31833, for example. Such a thermophilic bacterium-derived endoglucanase can be used as a "parent endoglucanase.". A parent endoglucanase preferably comprises the amino acid sequence shown in SEQ ID NO: 1, 7, 13, 19, 25, 31 or 37. Examples of the parent endoglucanase include a protein having a deletion, a substitution, an addition, or an insertion of one or a plurality of or one or several amino acids with respect to the amino acid sequence shown in SEQ ID NO: 1, 7, 13, 19, 25, 31, or 37, and having endoglucanase activity. The range of "1 or several" is not particularly limited and it is 10 or less, and further preferably 5 or less, particularly preferably 4 or less, or 1 or 2, for example.

Moreover, examples of a parent endoglucanase also include a protein containing and preferably comprising an amino acid sequence that has 90%, 95%, 99% or more identity with the amino acid sequence shown in SEQ ID NO: 1, 7, 13, 19, 25, 31 or 37 when calculated using BLAST (Basic Local Alignment Search Tool at the National Center for Biological Information (NCBI)) or the like (e.g., default; that is, initially set parameters), and having endoglucanase activity.

The term "identity" refers to the percentage of amino acid residues identical to and amino acid residues analogous to the other amino acid residues in all the amino acid residues overlapped when an optimum alignment is performed by introducing gaps or no gaps into two amino acid sequences and then aligning the two amino acid sequences. Such an identity can be found using a method known by persons skilled in the art, sequence analysis software, and the like (a known algorithm such as BLAST or FASTA). The term "endoglucanase activity" is as defined above and can be determined by adding an enzyme solution to a substrate solution of phosphoric acid swollen cellulose that has been dissolved in 50 mM acetic acid-sodium acetate buffer (pH 5.2) or the like, performing 1 hour of reaction at 30° C. to 85° C., stopping the reaction by changing the pH if necessary, and then determining the concentration of glucose in the reaction solution using a glucose determination kit, for example.

The term "mutant endoglucanase" refers to a protein characterized in that in the amino acid sequence of the above parent endoglucanase, an amino acid residue corresponding to the 273rd tryptophan in the amino acid sequence of SEQ ID NO: 1 is substituted with an amino acid selected from amino acids other than aromatic amino acids, and the protein has endoglucanase activity.

As described in detail in the following examples, we found by crystal structure analysis that in the amino acid sequence of the parent endoglucanase; that is, the amino acid sequence shown in SEQ ID NO: 1 (the amino acid sequence shown in SEQ ID NO: 1 comprises a total of 73 aromatic amino acid residues consisting of 19 tryptophans, 20 phenyl alanines, 11 histidines, and 23 tylosins), the 273rd tryptophan located in the vicinity of the active site establishes the hydrophobic interaction with coniferylaldehyde. Specifically, it has been revealed that the amino acid establishes hydrophobic interaction with a lignin-derived aromatic compound in the vicinity of the active site, and is strongly involved in the inhibition of a hydrolytic reaction of cellulose that is a substrate for endoglucanase. The object of introducing a mutation into endoglucanase is to disrupt the hydrophobic interaction involved in activity inhibition to suppress the incorporation of the lignin-derived aromatic compound in the vicinity of the active site.

The expression "an amino acid corresponding to the 273rd tryptophan in the amino acid sequence of SEQ ID NO: 1" refers to, when the amino acid sequence of the above parent endoglucanase is compared with the amino acid sequence of SEQ ID NO: 1 in terms of conformation, the amino acid that is located at a position (in the amino acid sequence of the above thermophilic bacterium-derived endoglucanase) similar to that of the 273rd tryptophan in the amino acid sequence of SEQ ID NO: 1, and is involved in the establishment of hydrophobic interaction with a lignin-derived aromatic compound. The type of amino acid as specified by the expression "amino acid corresponding to the 273rd tryptophan in the amino acid sequence of SEQ ID NO: 1" is preferably tryptophan.

A method of determining such "amino acid corresponding to the 273rd tryptophan in the amino acid sequence of SEQ ID NO: 1" can be performed by the following procedures 1) to 3):

Procedure 1) In the amino acid sequence of the *Pyrococcus horikoshi*-derived endoglucanase (hereinafter, described as "EGPh") shown in SEQ ID NO: 1, the position of initiating methionine is defined as position 1. Regarding portions following the amino acid sequence, amino acid residues are numbered in order such as position 2, 3, 4 . . . and tryptophan at position 273 is defined as the 273rd tryptophan in SEQ ID NO: 1. Procedure 2) Next, an amino acid in the amino acid sequence of a parent endoglucanase, corresponding to the 273rd tryptophan in the amino acid sequence shown in SEQ ID NO: 1, is determined. The amino acid position corresponding thereto can be revealed by aligning the amino acid sequence of the parent endoglucanase (in particular, an amino acid sequence in the vicinity of the active site) with the amino acid sequence of SEQ ID NO: 1. Such procedure is referred to as amino acid sequence alignment and performed using many well-known software products such as ClustalW as alignment tools and default parameters. Persons skilled in the art can reveal the position of an amino acid of the parent endoglucanase, corresponding to the 273rd tryptophan in the amino acid sequence shown in SEQ ID NO: 1 by performing alignment between amino acid sequences having different lengths.

Procedure 3) The amino acid located at the position corresponding to the 273rd tryptophan in the amino acid sequence shown in SEQ ID NO: 1, as revealed by the above alignment analysis, is determined to be the "amino acid corresponding to the 273rd tryptophan in the amino acid sequence shown in SEQ ID NO: 1," in the parent endoglucanase.

When the above parent endoglucanase contains a mutation such as a deletion, an addition, or an insertion of an amino acid at a position that is not the one described in the above "amino acid corresponding to the 273rd tryptophan in the amino acid sequence shown in SEQ ID NO: 1," such a position of "amino acid corresponding to the 273rd tryptophan in the amino acid sequence shown in SEQ ID NO: 1" that we found by counting from the N-terminus may not be the 273rd position. Even in such a case, the "amino acid corresponding to the 273rd tryptophan in the amino acid sequence shown in SEQ ID NO: 1" determined by the above method is substituted with an amino acid other than aromatic amino acids, thereby obtaining our mutant endoglucanase.

As an amino acid selected from those other than aromatic amino acids, any amino acid can be used, as long as it is not an aromatic amino acid residue such as tryptophan, tylosin, phenyl alanine, and histidine. Examples of an amino acid residue that can be used for substitution include lysine (Lys), arginine (Arg), histidine (His), glutamic acid (Glu), aspartic acid (Asp), valine (Val), isoleucine (Ile), threonine (Thr), serine (Ser), cysteine (Cys), methionine (Met), glutamine (Gln), asparagine (Asn), glycine (Gly), leucine (Leu), and preferably alanine (Ala). Furthermore, if a protein retaining endoglucanase activity can be produced as a result of artificial deletion of the above amino acid corresponding to the 273rd tryptophan in the amino acid sequence shown in SEQ ID NO: 1, the amino acid corresponding to the 273rd tryptophan in the amino acid sequence shown in SEQ ID NO: 1 can be artificially deleted.

Particularly preferably, the mutant endoglucanase comprises the amino acid sequence shown in SEQ ID NO: 2, 8, 14, 20, 26, 32, or 38.

The mutant endoglucanase can be produced using known techniques. For example, the mutant endoglucanase can be produced by introducing a mutation into a gene encoding the amino acid sequence of a parent endoglucanase, preparing a mutant gene encoding a mutant endoglucanase, and then causing the expression of the mutant gene using an appropriate host. Examples of the "gene" include nucleic acids such as DNA, RNA, and DNA/RNA hybrids.

A mutant gene encoding a mutant endoglucanase can be prepared using a known mutagenesis method.

When a mutant endoglucanase is prepared using EGPh as a parent endoglucanase, for example, a gene encoding EGPh can be cloned from cells of *Pyrococcus horikoshii* (registration No. JCM9974, JCM (Japan Collection of Microorganisms) Catalogue of Strains, 7th edition, issued on January 1999).

When a mutant endoglucanase is prepared using another endoglucanase having a conformation analogous to that of EGPh as a parent endoglucanase, the parent endoglucanase gene can be cloned from the cells of a microorganism or the like that produces the endoglucanase protein (such as *Ign-*

*isphaera aggregans, Staphylothermus hellenicus, Pyrococcus abyssi, Acidthermus cellulolyticus*, and *Spirochaeta thermophile*).

A gene encoding a parent endoglucanase can be obtained by isolating DNA from one of these microorganisms having endoglucanases according to a known method, and then performing DNA amplification by a technique such as PCR. For example, such a gene can be obtained by culturing *Pyrococcus horikoshii*, finding by the BLAST search method a gene (e.g., SEQ ID NO: 1) that has a sequence analogous to that of the endoglucanase of *Pyrococcus horikoshii* and thus is thought to exhibit the enzyme activity, and then amplifying by PCR and extracting the gene from the gene sequence.

A mutation is artificially caused to take place at a predetermined site of a parent endoglucanase gene obtained from the above endoglucanase-producing bacteria, and thus a mutant endoglucanase gene is prepared. When a mutant endoglucanase gene characterized by a decreased degree of activity inhibition by a lignin-derived aromatic compound is prepared, an artificial mutation is caused to take place in a parent endoglucanase so that the above amino acid corresponding to the 273rd tryptophan in the amino acid sequence shown in SEQ ID NO: 1 is substituted.

A method of site-directed mutagenesis by which a mutation is caused to take place at a target site of a gene can be performed by conventional PCR that is usually employed.

The above-prepared gene encoding the mutant endoglucanase is ligated to a site downstream of a promoter in an appropriate expression vector using a restriction enzyme and DNA ligase, and thus the expression vector containing the gene can be produced. Examples of an expression vector include bacterial plasmids, yeast plasmids, phage DNA (e.g., lambda phages), the DNA of a virus such as retrovirus, baculovirus, vaccinia virus, and adenovirus, derivatives or the like of SV40, and *agrobacterium* as a vector for plant cells. Any vector can be used herein as long as it is replicable and can survive in host cells. For example, when a host is *Escherichia coli*, examples thereof include pUS, pET, and pBAD. When a host is yeast, examples thereof include pPink-HC, pPink-LC, pPinkα-HC, pPicZ, pPicα, pPic6, pPic6α, pFLD1, pFLD1α, pGAPZ, pGAPZα, pPic9K, and pPic9.

Any promoter can be used herein, as long as it is appropriate and compatible with a host to be used for gene expression. For example, when a host is *Escherichia coli*, examples thereof include a lac promoter, a Trp promoter, a PL promoter, and a PR promoter. When a host is yeast, examples of thereof include an AOX1 promoter, a TEF1 promoter, an ADE2 promoter, a CYC1 promoter, and a GAL-L1 promoter.

Examples of host cells preferably include *Escherichia coli*, bacterial cells, yeast cells, fungal cells, insect cells, plant cells, and animal cells. Examples of yeast cells include the genus *Pichia*, the genus *Saccharomyces*, and the genus *Schizosaccharomyces*. Examples of fungal cells include the genus *Aspergillus* and the genus *Trichoderma*. Examples of insect cells include Sf9 and the like. Examples of plant cells include dicotyledons and the like. Examples of animal cells include CHO, HeLa and HEK293.

Transformation or transfection can be performed by a known method such as a calcium phosphate method and electroporation. The mutant endoglucanase can be obtained by causing the expression under the control of a promoter in host cells transformed or transfected as described above and then recovering the product. Upon expression, transformed or transfected host cells are proliferated or grown to appropriate cell density, a promoter is induced to act by temperature shift or chemical means for induction such as addition of isopropyl-1-thio-β-D-galactoside (IPTG), for example, and then cells are further cultured for a predetermined period.

When a mutant endoglucanase is discharged outside the cells, it is directly purified from a medium. When a mutant endoglucanase is present outside the cells, it is purified after disruption of cells by physical means such as ultrasonication or mechanical disruption or chemical means such as a cytolytic agent. The mutant endoglucanase can be partially or completely purified from a medium of recombinant cells using a combination of techniques such as ammonium sulfate or ethanol precipitation, acid extraction, anion or cation exchange chromatography, reverse phase high performance liquid chromatography, affinity chromatography, gel filtration chromatography, and electrophoresis.

The mutant endoglucanase is characterized by a significantly decreased degree of activity inhibition by a lignin-derived aromatic compound, compared with the parent endoglucanase. Therefore, the mutant endoglucanase has endoglucanase activity that is approximately 2-fold, 3-fold, 4-fold, 5-fold, 6-fold, 7-fold, 8-fold, 9-fold, 10-fold, 11-fold, 12-fold, 13-fold, 14-fold, 15-fold or more stronger than that of the parent endoglucanase in the presence of a lignin-derived aromatic compound.

The mutant endoglucanase may be the one purified or partially purified.

Furthermore, the mutant endoglucanase may be immobilized on a solid phase. Examples of a solid phase include a polyacrylamide gel, a polystyrene resin, porous glass, and a metallic oxide (but are not particularly limited thereto). Immobilization of the mutant endoglucanase to a solid phase is advantageous in that it enables continuous and repeated use thereof.

Moreover, treated products of cells transformed with a gene encoding the above mutant endoglucanase can also be used as a partially purified mutant endoglucanase. Examples of the "treated products of transformed cells" include transformed cells immobilized on a solid phase, dead and disrupted cells of the transformed cells and these cells immobilized on a solid phase.

The mutant endoglucanase is mixed with cellulase, and thus the mixture can be used as an enzyme composition for degrading biomass to hydrolyze cellulose-containing biomass. The term "cellulase" to be used herein is not particularly limited, as long as it is an enzyme having activity to degrade cellulose, and may also be a mixture of one or more types thereof. Examples of such an enzyme include cellulase, hemicellulase, cellobiohydrolase, endoglucanase, exoglucanase, β-glucosidase, xylanase, mannanase, xyloglucanase, chitinase, chitosanase, and galactanase. Preferably, cellulase is filamentous bacterium-derived cellulase.

Examples of a microorganism producing filamentous bacterial cellulase include the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor*, and the genus *Talaromyces*. These microorganisms produce cellulase in a culture solution and then the culture solution can be directly used as unpurified filamentous bacterial cellulase, or the culture solution is purified and formulated and then the product can be used as a filamentous bacterial cellulase mixture. When a filamentous bacterial cellulase mixture is purified from the above culture solution, formulated, and then used, a substance other than enzymes such as a protease inhibitor, a dispersing agent, a dissolution promoter, or a stabilizer is added to the filamentous bacterial cellulase mixture, and then the resultant can also be used as a cellulase preparation.

Filamentous bacterium-derived cellulase is preferably the genus *Trichoderma*-derived cellulase. Such genus *Trichoderma*-derived cellulase is not particularly limited, as long as it is an enzyme having activity to degrade cellulose, and may also be a mixture of one or more types thereof. Examples of such an enzyme include cellulase, hemicellulase, cellobiohydrolase, endoglucanase, exoglucanase, β-glucosidase, xylanase, mannanase, xyloglucanase, chitinase, chitosanase, and galactanase. A more preferable example of the genus *Trichoderma*-derived cellulase is a *Trichoderma reesei*-derived cellulase mixture. Examples of the *Trichoderma reesei*-derived cellulase mixture include a *Trichoderma reesei* ATCC66589-derived cellulase mixture, a *Trichoderma reesei* QM9414-derived cellulase mixture, a *Trichoderma reesei* QM9123-derived cellulase mixture, a *Trichoderma reesei* RutC-30-derived cellulase mixture, a *Trichoderma reesei* PC3-7-derived cellulase mixture, a *Trichoderma reesei* CL-847-derived cellulase mixture, a *Trichoderma reesei* MCG77-derived cellulase mixture, a *Trichoderma reesei* MCG80-derived cellulase mixture, and a *Trichoderma viride* QM9123-derived cellulase mixture. Moreover, a strain to be used herein may also be a genus *Trichoderma*-derived mutant strain prepared by mutation treatment using an agent for mutation, ultraviolet irradiation, or the like to have improved cellulase productivity.

The above-obtained mutant endoglucanase alone or the same combined with cellulase can be used for foods, feedstuffs, detergents, treatment of cellulose-containing fabric, and production of a sugar solution from cellulosic biomass.

The above foods and feedstuffs contain at least the mutant endoglucanase, and further contain other ingredients as necessary. The content of the mutant endoglucanase in the above foods or feedstuff is not particularly limited and adequately selected depending on the purpose. Moreover, methods of producing the above foods and feedstuffs are not particularly limited and can be adequately selected depending on the purpose. In addition, the above foods and feedstuffs contain the mutant endoglucanase and, thus, they can degrade cellulose and the like contained in foods and feedstuffs, for example, enabling efficient digestion.

The content of the mutant endoglucanase in the above detergent is not particularly limited and can be adequately selected depending on the purpose. Moreover, a method of producing the above detergent is not particularly limited and can be adequately selected depending on the purpose. The above detergent contains the mutant endoglucanase and, thus, dirt tangling in the cellulose fibers of an object to be cleaned can be efficiently removed, for example.

A method of treating the above cellulose-containing fabric comprises a step of treating (treatment step) cellulose-containing fabric using the mutant endoglucanase, and other steps if necessary. The above cellulose-containing fabric is not particularly limited and can be adequately selected depending on the purpose, such as jeans. Moreover, the amount of the mutant endoglucanase to be used, along with the temperature, time, and the like in the above treatment step are not particularly limited and can be adequately selected depending on the purpose. For example, the above jeans can be treated by the above method for treating cellulose-containing fabric so that stone washing treatment can be performed, for example.

Cellulose-containing biomass is not limited, as long as it contains at least cellulose. Specific examples thereof include bagasse, corn stover, corncobs, switch glass, rice straw, wheat straw, tree, wood, waste construction materials, newspaper, waste paper, and pulp. These examples of cellulose-containing biomass contain impurities such as an aromatic macromolecular compound, lignin, and hemicellulose. Cellulose-containing biomass is subjected to pre-treatment by which lignin and hemicellulose are partially degraded using acid, alkali, pressurized hot water, or the like, and then the resultant can be used as cellulose.

A cellulose-containing biomass suspension contains the above cellulose-containing biomass at a solid content concentration of 0.1%-30%. A solvent to be used for suspension is not particularly limited and can be adequately selected depending on the purpose.

The term "addition" refers to the addition of a mutant endoglucanase, a treated product of transformed cells, cellulase, or the like to a cellulose-containing biomass suspension. The amount thereof to be added is not particularly limited and can be adequately selected depending on the purpose. For example, the amount thereof to be added per gram of the above cellulose-containing biomass preferably ranges from 0.001 mg to 100 mg, more preferably ranges from 0.01 mg to 10 mg, and particularly preferably ranges from 0.1 mg to 1 mg.

The temperature for enzymatic treatment of a cellulose-containing biomass suspension in the production of a sugar solution is not particularly limited. The reaction temperature preferably ranges from 30° C. to 100° C., more preferably ranges from 40° C. to 90° C., and particularly preferably ranges from 50° C. to 80° C. The pH for treatment is not particularly limited and preferably ranges from pH2 to pH8, more preferably ranges from pH3 to pH7, and particularly preferably ranges from pH4 to pH6. The concentration of the solid content of cellulose-containing biomass preferably ranges from 0.1% to 30%.

The concentration of the solid content thereof is determined within the above range to maximize the degradation efficiency of the enzyme composition for degrading biomass. The enzymatic treatment may be performed in either a batch mode or a continuous mode. A hydrolysate resulting from such enzymatic treatment contains monosaccharide components such as glucose and xylose, and thus it can be used as a raw-material sugar for ethanol, lactic acid, and the like.

EXAMPLES

Our mutant endoglucanase and methods are hereafter described in greater detail with reference to the following examples, although this disclosure is not limited thereto.

Example 1

Determination of the 273Rd Amino Acid Residue in Thermophilic Bacterium-Derived Endoglucanase A BLAST search was performed to search for a thermophilic bacterium-derived endoglucanase having high identity with the amino acid sequence of EGPh.

Protein BLAST was used to perform a BLAST search using SEQ ID NO: 1 as a query. As a result, it was confirmed that the *Ignisphaera aggregans*-derived endoglucanase1 (EGIa1) described in SEQ ID NO: 7, the *Ignisphaera aggregans*-derived endoglucanase 2 (EGIa2) described in SEQ ID NO: 13, the *Staphylothermus hellenicus*-derived endoglucanase (EGSh) described in SEQ ID NO: 19, the *Pyrococcus abyssi*-derived endoglucanase (EGPa) described in SEQ ID NO: 25, the *Acidthermus cellulolyticus*-derived endoglucanase (EGAc) described in SEQ ID NO: 31, and the *Spirochaeta thermophile*-derived endoglucanase (EGSt)

described in SEQ ID NO: 37 are appropriate as thermophilic bacterium-derived endoglucanases exhibiting 75% or more identity with EGPh.

Alignment of EGPh with the thermophilic bacterium-derived endoglucanases described in SEQ ID NOs: 7, 13, 19, 25, 31, and 37 was performed using ClustalW, which is a well known software product. As a result, the amino acid located at the position corresponding to that of tryptophan at position 273 in the amino acid sequence shown in SEQ ID NO: 1 was determined to be located at position 273 in the thermophilic bacterium-derived endoglucanases described in SEQ ID NOs: 7, 13, 19, 25, 31, and 37, and it is underlined in FIGS. 1-1 to 1-4.

Reference Example 1

Preparation of Parent Endoglucanase

EGPh, EGIa1, EGIa2, EGSh, EGPa, EGAc, and EGSt genes described in SEQ ID NOs: 1, 7, 13, 19, 25, 31, and 37, respectively, were fully synthesized, ligated to Nco I and BamH I of pET 11d using a "Mighty Mix" DNA Ligation Kit (Takara Bio Inc.), and then the resultants were transformed into JM109 (Takara Bio Inc.). Screening was performed using LB agar medium containing ampicillin as an antibiotic. The prepared vectors (pET-EGPh, EGAIa1, EGAIa2, EGSh, EGPa, EGAc, and EGSt) were isolated from the transformed JM109 strain using a Mini-Prep kit (QIAGEN), and then nucleotide sequence analysis was performed. pET-EGPh, EGAIa1, EGAIa2, EGSh, EGPa, EGAc, and EGSt were transformed into the *Escherichia coli* BL21 (DE3) pLysS strain for expression, and thus BL21-PfuBGL strains were prepared. Each BL21-PfuBGL strain was inoculated into 10 mL of an ampicillin-containing LB medium and then cultured overnight at 37° C. with shaking (preculture). As a main culture, cells obtained by the preculture were inoculated into 1 L of an ampicillin-containing LB medium, and then shake culture was performed until absorbance (OD600) at a wavelength of 600 nm reached 0.6. Thereafter, isopropyl-1-thio-β-D-galactoside (IPTG) was added to the final concentration of 0.5 mM, followed by overnight culture at 25° C. After culture, cells were collected by centrifugation and then suspended again in 50 mM potassium phosphate buffer (pH 7.0). This solution was subjected to ultrasonication while the solution was cooled with ice. The supernatant was collected as a cell-free extract by centrifugation. The thus obtained cell-free extract was maintained at 85° C. for 15 minutes, and *Escherichia coli*-derived proteins other than the endoglucanase were coagulated and precipitated. The precipitate was removed by centrifugation. The supernatant was dialyzed against 50 mM acetate buffer (pH 5.0) using a dialysis membrane made of regenerated cellulose with a molecular weight cut-off of 10000 (Spectrum Laboratories). The thus obtained protein solutions were used as wild-type EGPh, EGAIa1, EGAIa2, EGSh, EGPa, EGAc, and EGSt.

Example 2

Preparation of Mutant Endoglucanase

The mutant endoglucanases were prepared by the following techniques using primer pairs listed in Table 1.

TABLE 1

| Enzyme to be mutated | Nucleotide sequence (5'→3') | SEQ ID NO: |
|---|---|---|
| EGPh | GGCTACAACGCTTGGGCGGGAGGAAATCTAATG | SEQ ID NO: 5 |
| | CATTAGATTTCCTCCCGCCCAAGCGTTGTAGCC | SEQ ID NO: 6 |
| EGIa1 | TCATATTATGTATTTGCGGGAGAAAATCTTAGG | SEQ ID NO: 11 |
| | CCTAAGATTTTCTCCCGCAAATACATAATATGA | SEQ ID NO: 12 |
| EGIa2 | CCCGAGGCTACCTACGCGGGTGAGAATCTCAGA | SEQ ID NO: 17 |
| | TCTGAGATTCTCACCCGCGTAGGTAGCCTCGGG | SEQ ID NO: 18 |
| EGSh | CCTTATTCCTGCTTCGCGGGAGAAAACTTAATG | SEQ ID NO: 23 |
| | CATTAAGTTTTCTCCCGCGAAGCAGGAATAAGG | SEQ ID NO: 24 |
| EGPa | GGATGGTGGACTTTCGCGGGAGAGAACTTAATG | SEQ ID NO: 29 |
| | CATTAAGTTCTCTCCCGCGAAAGTCCACCATCC | SEQ ID NO: 30 |
| EGAc | GGAGACTCCTACTGGGCGGGCGGCAACCTGCAA | SEQ ID NO: 35 |
| | TTGCAGGTTGCCGCCCGCCCAGTAGGAGTCTCC | SEQ ID NO: 36 |
| EGSt | GGCGATACCTACTGGGCGGGCGGCAATCTCAAA | SEQ ID NO: 41 |
| | TTTGAGATTGCCGCCCGCCCAGTAGGTATCGCC | SEQ ID NO: 42 |

Oligonucleotides represented by the nucleotide sequences of SEQ ID NOs: 5 and 6 were used for the gene encoding the amino acid sequence shown in SEQ ID NO: 1, and thus mutant EGPh (SEQ ID NO: 2) was prepared using site-directed mutagenesis. Similarly, oligonucleotides represented by the nucleotide sequences shown in SEQ ID NOs: 11 and 12 were used for the gene encoding the amino acid sequence shown in SEQ ID NO: 7, and thus mutant EGIa1 (SEQ ID NO: 8) was prepared. SEQ ID NOs: 17 and 18 were used for the gene encoding the amino acid sequence shown in SEQ ID NO: 13, and thus mutant EgIa2 (SEQ ID NO: 14) was prepared. SEQ ID NOs: 23 and 24 were used for the gene encoding the amino acid sequence shown in SEQ ID NO: 19, and thus mutant EGSh (SEQ ID NO: 20) was prepared. SEQ ID NOs: 29 and 30 were used for the gene encoding the amino acid sequence shown in SEQ ID NO: 25, and thus mutant EGPa (SEQ ID NO: 26) was prepared. SEQ ID NOs: 35 and 36 were used for the gene encoding the amino acid sequence shown in SEQ ID NO: 31, and thus mutant EGAc (SEQ ID NO: 32) was prepared. SEQ ID NOs: 41 and 42 were used for the gene encoding the amino acid sequence shown in SEQ ID NO: 37, and thus mutant EGSt (SEQ ID NO: 38) was prepared. After confirmation of the sequences of the obtained genes, the genes were expressed in *Escherichia coli* by the procedures described in Reference Example 1. It was successfully confirmed that the EGPh mutant, the EGAIa1 mutant, the EGAIa2 mutant, the EGSh mutant, the EGPa mutant, the EGAc mutant, and the EGSt mutant can all be expressed as heteroproteins in *Escherichia coli*.

Reference Example 2

Preparation of Phosphoric Acid Swollen Cellulose

Phosphoric acid swollen cellulose to be used as a substrate upon measurement of the hydrolysis activity of endoglucanase was prepared from Avicel according to the method described in Walseth (1971) Tappi 35: 228 (1971) and Wood Biochem J. 121: 353 (1971). This substance was diluted using buffer and water to obtain a 2 wt % mixture so that the final concentration of sodium acetate was 50 mM (pH 5.2). This was designated as phosphoric acid swollen cellulose and used for the following examples.

Example 3

Activity of Mutants to Degrade Phosphoric Acid Swollen Cellulose

The mutants obtained in Example 2 and the parent endoglucanases prepared in Reference Example 1 were compared in terms of their activity to degrade phosphoric acid swollen cellulose in the following experiment, where 1% phosphoric acid swollen cellulose/50 mM acetate buffer (pH 5.2) was used as a substrate. The enzymes prepared in Reference Example 1 and Example 2 were each added at a final concentration of 0.5 µM, followed by 1 hour of enzymatic reaction at 50° C. The concentration of glucose (g/L) generated by each parent endoglucanase under the above reaction conditions was determined to be 100%. The activity of each mutant to degrade phosphoric acid swollen cellulose is listed in Table 2 in terms of the relative value.

TABLE 2

| Enzyme | Wild-type/Mutant | Relative activity |
| --- | --- | --- |
| EGPh | Wild-type | 100% |
|  | Mutant | 100% |
| EGIa1 | Wild-type | 100% |
|  | Mutant | 100% |
| EGIa2 | Wild-type | 100% |
|  | Mutant | 100% |
| EGSh | Wild-type | 100% |
|  | Mutant | 100% |
| EGPa | Wild-type | 100% |
|  | Mutant | 100% |
| EGAc | Wild-type | 100% |
|  | Mutant | 100% |
| EGSt | Wild-type | 100% |
|  | Mutant | 100% |

It was confirmed that there were no difference between each parent endoglucanase and the relevant mutant at 50° C.

Example 4

Inhibition Experiment 1 Using Lignin-Derived Aromatic Compound

The activity of the wild-type and the mutant endoglucanases to degrade phosphoric acid swollen cellulose in the presence of coniferyl aldehyde was measured. 1% phosphoric acid swollen cellulose/50 mM acetate buffer (pH 5.2) was used as a substrate. Coniferyl aldehyde (Sigma Aldrich) was added at final concentrations of 0, 5, 10, and 15 mM. The enzymes prepared in Reference Example 1 and Example 2 were each added at a final concentration of 0.5 µM, followed by 1 hour of enzymatic reaction at 50° C. The concentration of glucose (g/L) generated by each parent endoglucanase when the concentration of coniferyl aldehyde added had been 0 mM was determined to be 100%. The activity of each mutant to degrade phosphoric acid swollen cellulose is listed in Table 3 in terms of the relative value.

TABLE 3

| | | Concentration of coniferyl aldehyde added | | | |
| --- | --- | --- | --- | --- | --- |
| Enzyme | | 0 mM | 5 mM | 10 mM | 15 mM |
| EGPh | Wild-type | 100% | 60% | 30% | 5% |
|  | Mutant | 100% | 90% | 80% | 70% |
| EGIa1 | Wild-type | 100% | 70% | 35% | 10% |
|  | Mutant | 100% | 95% | 95% | 90% |
| EGIa2 | Wild-type | 100% | 65% | 35% | 10% |
|  | Mutant | 100% | 89% | 85% | 80% |
| EGSh | Wild-type | 100% | 55% | 30% | 5% |
|  | Mutant | 100% | 89% | 80% | 70% |
| EGPa | Wild-type | 100% | 55% | 30% | 10% |
|  | Mutant | 100% | 95% | 90% | 70% |
| EGAc | Wild-type | 100% | 65% | 35% | 10% |
|  | Mutant | 100% | 95% | 85% | 79% |
| EGSt | Wild-type | 100% | 60% | 30% | 5% |
|  | Mutant | 100% | 90% | 80% | 70% |

It was confirmed that the inhibition of the activity of each mutant was significantly decreased.

Example 5

Inhibition Experiment 2 Using Lignin-Derived Aromatic Compound

The activity of the wild-type and the mutant endoglucanases to degrade phosphoric acid swollen cellulose in the presence of vanillin was measured. 1% phosphoric acid swollen cellulose/50 mM acetate buffer (pH 5.2) was used as a substrate. Vanillin (Sigma Aldrich) was added at final concentrations of 0, 5, 10, and 15 mM. The enzymes prepared in Reference Example 1 and Example 2 were added at a final concentration of 0.5 µM, followed by 1 hour of enzymatic reaction at 50° C. The concentration of glucose (g/L) generated by each parent endoglucanase when the concentration of vanillin added had been 0 mM was determined to be 100%. The activity of each mutant to degrade phosphoric acid swollen cellulose is listed in Table 4 in terms of the relative value.

TABLE 4

| | | Concentration of vanillin added | | | |
| --- | --- | --- | --- | --- | --- |
| Enzyme | | 0 mM | 5 mM | 10 mM | 15 mM |
| EGPh | Wild-type | 100% | 40% | 40% | 40% |
|  | Mutant | 100% | 95% | 90% | 90% |
| EGIa1 | Wild-type | 100% | 60% | 55% | 40% |
|  | Mutant | 100% | 100% | 100% | 95% |
| EGIa2 | Wild-type | 100% | 50% | 45% | 40% |
|  | Mutant | 100% | 95% | 90% | 90% |
| EGSh | Wild-type | 100% | 40% | 35% | 30% |
|  | Mutant | 100% | 90% | 85% | 80% |
| EGPa | Wild-type | 100% | 40% | 40% | 40% |
|  | Mutant | 100% | 90% | 90% | 90% |

TABLE 4-continued

| | | Concentration of vanillin added | | | |
|---|---|---|---|---|---|
| Enzyme | | 0 mM | 5 mM | 10 mM | 15 mM |
| EGAc | Wild-type | 100% | 50% | 45% | 40% |
| | Mutant | 100% | 100% | 95% | 95% |
| EGSt | Wild-type | 100% | 50% | 50% | 45% |
| | Mutant | 100% | 100% | 100% | 90% |

It was confirmed that the inhibition of the activity of each mutant was significantly decreased.

Example 6

Inhibition Experiment 3 Using Lignin-Derived Aromatic Compound

The activity of the wild-type and the mutant endoglucanases to degrade phosphoric acid swollen cellulose was measured in the presence of ferulic acid. 1% phosphoric acid swollen cellulose/50 mM acetate buffer (pH 5.2) was used as a substrate. Ferulic acid (Sigma Aldrich) was added at final concentrations of 0, 5, 10, and 15 mM. The enzymes prepared in Reference Example 1 and Example 2 were each added at a final concentration of 0.5 µM, followed by 1 hour of enzymatic reaction at 50° C. The concentration of glucose (g/L) generated by each parent endoglucanase when the concentration of ferulic acid added had been 0 mM was determined to be 100%. The activity of each mutant to degrade phosphoric acid swollen cellulose is listed in Table 5 in terms of the relative value.

TABLE 5

| | | Concentration of ferulic acid added | | | |
|---|---|---|---|---|---|
| Enzyme | | 0 mM | 5 mM | 10 mM | 15 mM |
| EGPh | Wild-type | 100% | 60% | 50% | 50% |
| | Mutant | 100% | 100% | 100% | 95% |
| EGIa1 | Wild-type | 100% | 55% | 50% | 50% |
| | Mutant | 100% | 100% | 100% | 95% |
| EGIa2 | Wild-type | 100% | 60% | 60% | 55% |
| | Mutant | 100% | 95% | 90% | 90% |
| EGSh | Wild-type | 100% | 65% | 55% | 50% |
| | Mutant | 100% | 95% | 85% | 80% |
| EGPa | Wild-type | 100% | 60% | 50% | 50% |
| | Mutant | 100% | 95% | 90% | 90% |
| EGAc | Wild-type | 100% | 65% | 60% | 55% |
| | Mutant | 100% | 100% | 100% | 95% |
| EGSt | Wild-type | 100% | 50% | 45% | 40% |
| | Mutant | 100% | 100% | 100% | 90% |

It was confirmed that the inhibition of the activity of each mutant was significantly decreased.

Reference Example 3

Preparation of Lignocellulose

Phosphoric acid swollen celluloses 1-3 to be used as substrates for measuring the hydrolysis activity of endoglucanase were prepared as follows.

1. Preparation of Lignocellulose 1 (Treatment with Ammonia)

Rice straw was used as cellulose. The cellulose was added to a small reactor (Taiatsu Techno Corporation, TVS-N2 (30 ml)), and then cooled with liquid nitrogen. An ammonia gas was fed to the reactor, thereby completely immersing the sample in the liquid ammonia. The reactor was closed using its lid, and then left to stand at room temperature for 15 minutes. Subsequently, treatment was performed for 1 hour in an oil bath at 150° C. After treatment, the reactor was removed from the oil bath, an ammonia gas leak was immediately performed within a draft chamber. The reactor was vacuumed using a vacuum pump to 10 Pa for drying. The resultant was used as lignocellulose 1 in the following examples.

2. Preparation of Lignocellulose 2 (Treatment with Dilute Sulfuric Acid)

Rice straw was used as cellulose. Cellulose was immersed in a 1% aqueous sulfuric acid solution, and then autoclaved for 30 minutes at 150° C. (Nitto Koatsu Co. Ltd.). After treatment, the resultant was subjected to solid-liquid separation into an aqueous sulfuric acid solution (hereinafter, referred to as "dilute-sulfuric-acid-treated solution") and cellulose treated with sulfuric acid. Next, the cellulose treated with sulfuric acid was mixed and agitated with the dilute-sulfuric-acid-treated solution so that the solid content concentration was 10 wt %. Then the mixture was adjusted to around pH 5 using sodium hydroxide. The resultant was used as lignocellulose 2 for the following examples.

3. Preparation of Lignocellulose 3 (Hydrothermal Treatment)

Rice straw was used as cellulose. The cellulose was immersed in water, and then autoclaved with agitation at 180° C. for 20 minutes (Nitto Koatsu Co. Ltd.). Pressure at this time was 10 MPa. After treatment, a solution component (hereinafter, referred to as "hydrothermally treated solution") and the treated biomass component were subjected to solid-liquid separation by centrifugation (3000 G). The thus treated biomass component was used as lignocellulose 3 for the following examples.

Example 7

Saccharification 1 of Lignocellulose Using Enzyme Composition Comprising Filamentous Bacterium-Derived Cellulase Mixture and Mutant Endoglucanase The changes in the amount of glucose generated when the enzyme composition had been caused to act on lignocellulose substrates were compared. The substrates were prepared by suspending 5 wt % lignocelluloses (1 to 3) (prepared in Reference Example 3) in 50 mM acetate buffer (pH5.2). Reactions were performed at 50° C. for 24 hours. The concentrations of the generated glucose were measured after adequate sampling. As a filamentous bacterium-derived cellulase mixture, commercially available Trichoderma reesei-derived cellulase (Celluclast, Sigma) was used. As endoglucanases, the mutant endoglucanases prepared in Example 2 and the wild-type endoglucanases prepared in Reference Example 1 were separately used. The following quantities of enzymes were added: 1.0 mg/mL cellulase, and 0.1 mg/mL endoglucanase (in an amount one tenth that of the cellulase). As shown in Tables 6, 7, and 8, the concentrations (g/L) of glucose generated after 24 hours of reaction from lignocelluloses 1, 2, and 3 were compared.

TABLE 6

| Substrate: Lignocellulose 1 | | | |
|---|---|---|---|
| Enzyme | Celluclast + Wild-type | Celluclast + Mutant | Celluclast alone |
| EGPh | 12 g/L | 16 g/L | 11 g/L |
| EGIa1 | 11 g/L | 15 g/L | |

TABLE 6-continued

| | Substrate: Lignocellulose 1 | | |
|---|---|---|---|
| Enzyme | Celluclast + Wild-type | Celluclast + Mutant | Celluclast alone |
| EGIa2 | 11 g/L | 16 g/L | |
| EGSh | 12 g/L | 14 g/L | |
| EGPa | 12 g/L | 14 g/L | |
| EGAc | 11 g/L | 16 g/L | |
| EGSt | 11 g/L | 14 g/L | |

TABLE 7

| | Substrate: Lignocellulose 2 | | |
|---|---|---|---|
| Enzyme | Celluclast + Wild-type | Celluclast + Mutant | Celluclast alone |
| EGPh | 11 g/L | 15 g/L | 11 g/L |
| EGIa1 | 12 g/L | 15 g/L | |
| EGIa2 | 11 g/L | 16 g/L | |
| EGSh | 11 g/L | 15 g/L | |
| EGPa | 12 g/L | 16 g/L | |
| EGAc | 11 g/L | 14 g/L | |
| EGSt | 12 g/L | 15 g/L | |

TABLE 8

| | Substrate: Lignocellulose 3 | | |
|---|---|---|---|
| Enzyme | Celluclast + Wild-type | Celluclast + Mutant | Celluclast alone |
| EGPh | 12 g/L | 16 g/L | 11 g/L |
| EGIa1 | 11 g/L | 15 g/L | |
| EGIa2 | 11 g/L | 14 g/L | |
| EGSh | 12 g/L | 15 g/L | |
| EGPa | 11 g/L | 15 g/L | |
| EGAc | 11 g/L | 14 g/L | |
| EGSt | 11 g/L | 14 g/L | |

The cases of using the wild-type endoglucanases were compared with the cases of using the mutant endoglucanases. As a result, the amount of glucose generated after 24 hours of reaction from any of the lignocelluloses (1 to 3) was significantly increased in the cases of using the mutant endoglucanases, such that it was about 1.4 times that generated in the cases of using the wild-type endoglucanases.

Reference Example 4

Preparation of the Genus Trichoderma-Derived Cellulase

The genus Trichoderma-derived cellulase was prepared using the following method.
1. Preculture Corn steep liquor (2.5% (w/vol)), glucose (2% (w/vol)), ammonium tartrate (0.37% (w/vol)), ammonium sulfate (0.14% (w/vol)), potassium dihydrogenphosphate (0.2% (w/vol)), calcium chloride dihydrate (0.03% (w/vol)), magnesium sulfate heptahydrate (0.03% (w/vol)), zinc chloride (0.02% (w/vol)), iron chloride (III) hexahydrate (0.01% (w/vol)), copper sulfate (II) pentahydrate (0.004% (w/vol)), manganese chloride tetrahydrate (0.0008% (w/vol)), boric acid (0.0006% (w/vol)), and hexaammonium heptamolybdate tetrahydrate (0.0026% (w/vol)) were added to distilled water to the concentrations shown in parentheses. Then, 100 mL of the mixture was added to a 500-mL baffled Erlenmeyer flask, autoclaved for sterilization at 121° C. for 15 minutes, and then allowed to cool. Alternatively, PE-M and Tween 80 autoclaved for sterilization at 121° C. for 15 minutes were added (0.1% each). The preculture medium was inoculated with Trichoderma reesei ATCC66589 spores at 1×10$^7$ cells/ml, followed by shake culture at 28° C. and 180 rpm for 72 hours, thereby performing the preculture (shaker: TAITEC BIO-SHAKER BR-40LF).

2. Main Culture

Corn steep liquor (2.5% (w/vol)), glucose (2% (w/vol)), cellulose (Avicel) 10% (w/vol), ammonium tartrate (0.37% (w/vol)), ammonium sulfate (0.14% (w/vol)), potassium dihydrogenphosphate (0.2% (w/vol)), calcium chloride dihydrate (0.03% (w/vol)), magnesium sulfate heptahydrate (0.03% (w/vol)), zinc chloride (0.02% (w/vol)), iron chloride (III) hexahydrate (0.01% (w/vol)), copper sulfate (II) pentahydrate (0.004% (w/vol)), manganese chloride tetrahydrate (0.0008% (w/vol)), boric acid (0.0006% (w/vol)), and hexaammonium heptamolybdate tetrahydrate (0.0026% (w/vol)) were added to distilled water to the concentrations shown in parentheses. Then, 2.5 L of this mixture was added to a 5-L agitation jar (ABLE, DPC-2A), autoclaved for sterilization at 121° C. for 15 minutes, and then allowed to cool. Alternatively, PE-M and Tween80 autoclaved for sterilization at 121° C. for 15 minutes were added (0.1% each). Next, 250 mL of Trichoderma reesei ATCC 66589 pre-cultured in a liquid medium by the above method was inoculated and then cultured at 28° C. and 300 rpm for 96 hours with a ventilation amount of 1 vvm. After centrifugation, the supernatant was subjected to membrane filtration (Millipore, Stericup-GV, Material: PVDF).

Example 8

Saccharification 2 of Lignocellulose Using Enzyme Composition Comprising Filamentous Bacterium-Derived Cellulase Mixture and Mutant Endoglucanase Lignocelluloses (1-3) prepared in Reference Example 3 were used as substrates. The Trichoderma reesei culture solution prepared in Reference Example 4 was used as a filamentous bacterium-derived cellulase mixture. Lignocelluloses (1-3) were hydrolyzed in a manner similar to that in Example 7, except for the quantities of the enzymes added: cellulase (1.0 mg/mL); endoglucanase (0.1 mg/mL (in an amount one tenth that of the cellulase); and β-glucosidase (Novozyme 188) (0.01 mg/mL (in an amount one hundredth that of the cellulase).

As shown in Tables 9, 10, and 11, the concentrations (g/L) of glucose generated after 24 hours of reaction from lignocelluloses 1, 2, and 3 were compared.

TABLE 9

| | Substrate: Lignocellulose 1 | | |
|---|---|---|---|
| Enzyme | Culture solution + Wild-type | Culture solution + Mutant | Culture solution alone |
| EGPh | 9 g/L | 13 g/L | 8 g/L |
| EGIa1 | 8 g/L | 12 g/L | |
| EGIa2 | 8 g/L | 13 g/L | |
| EGSh | 9 g/L | 11 g/L | |
| EGPa | 9 g/L | 11 g/L | |
| EGAc | 8 g/L | 13 g/L | |
| EGSt | 8 g/L | 11 g/L | |

TABLE 10

Substrate: Lignocellulose 2

| Enzyme | Culture solution + Wild-type | Culture solution + Mutant | Culture solution alone |
|---|---|---|---|
| EGPh | 8 g/L | 12 g/L | 8 g/L |
| EGIa1 | 9 g/L | 12 g/L | |
| EGIa2 | 8 g/L | 13 g/L | |
| EGSh | 8 g/L | 12 g/L | |
| EGPa | 9 g/L | 13 g/L | |
| EGAc | 8 g/L | 11 g/L | |
| EGSt | 9 g/L | 12 g/L | |

TABLE 11

Substrate: Lignocellulose 3

| Enzyme | Culture solution + Wild-type | Culture solution + Mutant | Culture solution alone |
|---|---|---|---|
| EGPh | 10 g/L | 13 g/L | 8 g/L |
| EGIa1 | 8 g/L | 12 g/L | |
| EGIa2 | 8 g/L | 11 g/L | |
| EGSh | 9 g/L | 12 g/L | |
| EGPa | 8 g/L | 12 g/L | |
| EGAc | 8 g/L | 11 g/L | |
| EGSt | 8 g/L | 11 g/L | |

The cases of using the wild-type endoglucanases were compared with the cases of using the mutant endoglucanases. As a result, the amount of glucose generated after 24 hours of reaction from any one of the lignocelluloses (1 to 3) was significantly increased in the cases of using the mutant endoglucanases, such that it was about 1.4 times that generated in the cases of using the wild-type endoglucanases. It was revealed that not only the use of commercially available cellulase as in Example 7, but also the use of the *Trichoderma reesei* culture solution can exhibit an effect in mutagenesis.

Comparative Example 1

Preparation of Mutant Endoglucanase

In this Comparative Example, a mutant was prepared by substituting the 273rd tryptophan with another aromatic amino acid using primers listed in Table 12.

TABLE 12

| Enzyme to be mutated | Nucleotide sequence(5'→3') | SEQ ID NO: |
|---|---|---|
| EGPh (W273Y) | GGCTACAACGCTTGGTACGGAGGAAATCTAATG | SEQ ID NO: 43 |
| | CATTAGATTTCCTCCGTACCAAGCGTTGTAGCC | SEQ ID NO: 44 |
| EGPh (W273F) | GGCTACAACGCTTGGTTTGGAGGAAATCTAATG | SEQ ID NO: 45 |
| | CATTAGATTTCCTCCAAACCAAGCGTTGTAGCC | SEQ ID NO: 46 |
| EGPh (W273H) | GGCTACAACGCTTGGCATGGAGGAAATCTAATG | SEQ ID NO: 47 |
| | CATTAGATTTCCTCCATGCCAAGCGTTGTAGCC | SEQ ID NO: 48 |

Oligonucleotides represented by the nucleotide sequences shown in SEQ ID NOs: 43 and 44 were used for the gene encoding the amino acid sequence shown in SEQ ID NO: 1, and then EGPh (W273Y) (the 273rd tryptophan was substituted with tyrosine: SEQ ID NO: 49)) was prepared by site-directed mutagenesis. Similarly, oligonucleotides shown in SEQ ID NOs: 45 and 46 were used and thus EGPh (W273F) (the 73rd tryptophan was substituted with phenyl alanine: SEQ ID NO: 50) was prepared. Oligonucleotides shown in SEQ ID NO: 47 and 48 were used and then EGPh (W273H) (the 73rd tryptophan was substituted with histidine: SEQ ID NO: 51) was prepared. It was successfully confirmed that these mutants can all be expressed as heteroproteins in *Escherichia coli*.

Comparative Example 2

Activity of Mutants to Degrade Phosphoric Acid Swollen Cellulose

The mutants obtained in Comparative Example 1 were compared in terms of activity by a technique similar to that in Example 3. The concentration (g/L) of glucose generated by each parent endoglucanase under the above reaction conditions was determined to be 100%. The activity of each mutant to degrade phosphoric acid swollen cellulose is shown in Table 13 in terms of the relative value.

TABLE 13

| Enzyme | Wild-type/Mutant | Relative activity |
|---|---|---|
| EGPh | Wild-type | 100% |
| EGPh(W273Y) | Mutant | 100% |
| EGPh(W273F) | Mutant | 100% |
| EGPh(W273H) | Mutant | 100% |

It was confirmed that there was no difference in activity between each mutant and the parent endoglucanase at 50° C.

Comparative Example 3

Inhibition Experiment Using Lignin-Derived Aromatic Compound

The activity of the wild-type and the mutant endoglucanases in Comparative Example 1 to degrade phosphoric acid swollen cellulose in the presence of coniferylaldehyde was measured. This experiment was conducted by the same procedures as in Example 4. The activity of each mutant to degrade phosphoric acid swollen cellulose is shown in Table 14 in terms of the relative value.

TABLE 14

| Enzyme | | Concentration of coniferyl aldehyde added | | | |
|---|---|---|---|---|---|
| | | 0 mM | 5 mM | 10 mM | 15 mM |
| EGPh | Wild-type | 100% | 60% | 30% | 5% |

TABLE 14-continued

| Enzyme | Concentration of coniferyl aldehyde added | | | |
|---|---|---|---|---|
| | 0 mM | 5 mM | 10 mM | 15 mM |
| EGPh (W273Y) Mutant | 100% | 50% | 10% | 0% |
| EGPh (W273F) 変位型 | 100% | 50% | 10% | 0% |
| EGPh (W273H) Mutant | 100% | 55% | 10% | 5% |

It was confirmed that in the mutants of Comparative Example 1 (subjected to substitution of tryptophan with an aromatic amino acid like tryptophan), the activity inhibition was not improved compared with the wild-type. Specifically, it was revealed that the 273rd tryptophan should be substituted with an amino acid other than aromatic amino acids.

INDUSTRIAL APPLICABILITY

Our mutant endoglucanases can be used to produce a sugar solution with the use of lignocellulose. The mutant endoglucanases can significantly reduce the enzyme cost because of their effects of improving lignocellulose degradation efficiency, and thus they are industrially very beneficial.

The subject matter of all publications, patents, and patent applications cited herein are incorporated herein by reference in their entirety.

The invention claimed is:

1. A mutant endoglucanase comprising an amino acid sequence that has 90% or more sequence identity with an amino acid sequence selected from the group consisting of SEQ ID NO: 1, 7, 13, 19, 25, 31, and 37, wherein said mutant endoglucanase amino acid sequence has an amino acid residue corresponding to the 273rd tryptophan in the amino acid sequence of SEQ ID NO: 1 substituted with an amino acid selected from amino acids other than aromatic amino acids and wherein said mutant endoglucanase possesses endoglucanase activity.

2. The mutant endoglucanase according to claim 1, wherein the amino acid residue corresponding to the 273rd tryptophan in the amino acid sequence of SEQ ID NO: 1 is substituted with alanine.

3. The mutant endoglucanase according to claim 1, comprising the amino acid sequence shown in SEQ ID NO: 2, 8, 14, 20, 26, 32, or 38.

4. DNA encoding the mutant endoglucanase according to claim 1.

5. DNA according to claim 4, comprising the nucleotide sequence shown in SEQ ID NO: 4, 10, 16, 22, 28, 34, or 40.

6. An expression vector, comprising the DNA according to claim 4.

7. Transformed cells, which are prepared by transformation using the expression vector according to claim 6.

8. A method of producing a mutant endoglucanase, comprising:
   (1) culturing the transformed cells according to claim 7; and
   (2) purifying the mutant endoglucanase produced by the transformed cells.

9. A composition that degrades biomass comprising a mutant endoglucanase according to claim 1 or transformed cells according to claim 7.

10. A method of producing a sugar solution from cellulose-derived biomass, comprising adding the composition for degrading biomass according to claim 9 to a cellulose-containing biomass suspension and then hydrolyzing the cellulose-containing biomass.

11. The method according to claim 10, further comprising adding filamentous bacterium-derived cellulase.

12. The mutant endoglucanase according to claim 2, comprising the amino acid sequence shown in SEQ ID NO: 2, 8, 14, 20, 26, 32, or 38.

13. DNA encoding the mutant endoglucanase according to claim 2.

14. DNA encoding the mutant endoglucanase according to claim 3.

15. An expression vector, comprising the DNA according to claim 5.

* * * * *

SEQUENCE LISTING

<160> NUMBER OF SEQ ID NOS: 51

<210> SEQ ID NO 1
<211> LENGTH: 458
<212> TYPE: PRT
<213> ORGANISM: Pyrococcus horikoshii EGPh

<400> SEQUENCE: 1

```
Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
    50                  55                  60

Gly Val Asn Trp Phe Gly Phe Glu Thr Pro Asn His Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205

Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270

Trp Gly Gly Asn Leu Met Ala Val Lys Asp Tyr Pro Val Asn Leu Pro
```

```
                275                 280                 285
Arg Asn Lys Leu Val Tyr Ser Pro His Val Tyr Gly Pro Asp Val Tyr
290                 295                 300

Asn Gln Pro Tyr Phe Gly Pro Ala Lys Gly Phe Pro Asp Asn Leu Pro
305                 310                 315                 320

Asp Ile Trp Tyr His Phe Gly Tyr Val Lys Leu Glu Leu Gly Tyr
                325                 330                 335

Ser Val Val Ile Gly Glu Phe Gly Lys Tyr Gly His Gly Gly Asp
                340                 345                 350

Pro Arg Asp Val Ile Trp Gln Asn Lys Leu Val Asp Trp Met Ile Glu
                355                 360                 365

Asn Lys Phe Cys Asp Phe Phe Tyr Trp Ser Trp Asn Pro Asp Ser Gly
370                 375                 380

Asp Thr Gly Gly Ile Leu Gln Asp Asp Trp Thr Thr Ile Trp Glu Asp
385                 390                 395                 400

Lys Tyr Asn Asn Leu Lys Arg Leu Met Asp Ser Cys Ser Lys Ser Ser
                405                 410                 415

Ser Ser Thr Gln Ser Val Ile Arg Ser Thr Thr Pro Thr Lys Ser Asn
                420                 425                 430

Thr Ser Lys Lys Ile Cys Gly Pro Ala Ile Leu Ile Ile Leu Ala Val
                435                 440                 445

Phe Ser Leu Leu Leu Arg Arg Ala Pro Arg
450                 455

<210> SEQ ID NO 2
<211> LENGTH: 458
<212> TYPE: PRT
<213> ORGANISM: Pyrococcus horikoshii EGPh W273A

<400> SEQUENCE: 2

Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
                20                  25                  30

Tyr Gln Thr Pro Thr Gly Ile Tyr Tyr Glu Val Arg Gly Asp Thr Ile
                35                  40                  45

Tyr Met Ile Asn Val Thr Ser Gly Glu Glu Thr Pro Ile His Leu Phe
50                  55                  60

Gly Val Asn Trp Phe Gly Phe Glu Thr Pro Asn His Val His Gly
65                  70                  75                  80

Leu Trp Lys Arg Asn Trp Glu Asp Met Leu Gln Ile Lys Ser Leu
                85                  90                  95

Gly Phe Asn Ala Ile Arg Leu Pro Phe Cys Thr Glu Ser Val Lys Pro
                100                 105                 110

Gly Thr Gln Pro Ile Gly Ile Asp Tyr Ser Lys Asn Pro Asp Leu Arg
                115                 120                 125

Gly Leu Asp Ser Leu Gln Ile Met Glu Lys Ile Ile Lys Lys Ala Gly
                130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
                180                 185                 190
```

-continued

Val Ile Gly Ala Asp Leu Lys Asn Glu Pro His Ser Val Thr Ser Pro
            195                 200                 205

Pro Ala Ala Tyr Thr Asp Gly Thr Gly Ala Thr Trp Gly Met Gly Asn
        210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270

Ala Gly Gly Asn Leu Met Ala Val Lys Asp Tyr Pro Val Asn Leu Pro
        275                 280                 285

Arg Asn Lys Leu Val Tyr Ser Pro His Val Tyr Gly Pro Asp Val Tyr
    290                 295                 300

Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
                325                 330                 335

Ser Val Val Ile Gly Glu Phe Gly Gly Lys Tyr Gly His Gly Gly Asp
            340                 345                 350

Pro Arg Asp Val Ile Trp Gln Asn Lys Leu Val Asp Trp Met Ile Glu
        355                 360                 365

Asn Lys Phe Cys Asp Phe Phe Tyr Trp Ser Trp Asn Pro Asp Ser Gly
    370                 375                 380

Asp Thr Gly Gly Ile Leu Gln Asp Asp Trp Thr Thr Ile Trp Glu Asp
385                 390                 395                 400

Lys Tyr Asn Asn Leu Lys Arg Leu Met Asp Ser Cys Ser Lys Ser Ser
                405                 410                 415

Ser Ser Thr Gln Ser Val Ile Arg Ser Thr Thr Pro Thr Lys Ser Asn
            420                 425                 430

Thr Ser Lys Lys Ile Cys Gly Pro Ala Ile Leu Ile Ile Leu Ala Val
        435                 440                 445

Phe Ser Leu Leu Leu Arg Arg Ala Pro Arg
    450                 455

<210> SEQ ID NO 3
<211> LENGTH: 1377
<212> TYPE: DNA
<213> ORGANISM: Pyrococcus horikoshii EGPh

<400> SEQUENCE: 3
atggagggga atactattct taaaatcgta ctaatttgca ctattttagc aggcctattc      60
gggcaagtcg tgccagtata tgcagaaaat acaacatatc aaacaccgac tggaatttac     120
tacgaagtga gaggagatac gatatacatg attaatgtca ccagtggaga ggaaactccc     180
attcatctct tggtgtaaa ctggtttggc tttgaaacac taatcatgt agtgcacgga      240
ctttggaaga gaaactggga agacatgctt cttcagatca aaagcttagg cttcaatgca     300
ataagacttc ctttctgtac tgagtctgta aaaccaggaa cacaaccaat tggaatagat     360
tacagtaaaa atccagatct tcgtggacta gatagcctac agattatgga aaagatcata     420
aagaaggccg agatcttgg tatctttgtc ttactcgact atcataggat aggatgcact      480
cacatagaac ccctctggta cacggaagac ttctcagagg aagactttat taacacatgg     540
atagaggttg ccaaaaggtt cggtaagtac tggaacgtaa taggggctga tctaaagaat     600

```
gagcctcata gtgttacctc acccccagct gcttatacag atggtaccgg ggctacatgg      660
ggtatgggaa accctgcaac cgattggaac ttggcggctg agaggatagg aaaagcgatt      720
ctgaaggttg cccctcattg gttgatattc gtggaggga cacaatttac taatccgaag      780
actgacagta gttacaaatg gggctacaac gcttggtggg gaggaaatct aatggccgta      840
aaggattatc cagttaactt acctaggaat aagctagtat acagccctca cgtatatggg      900
ccagatgtct ataatcaacc gtactttggt cccgctaagg gttttccgga taatcttcca      960
gatatctggt atcaccactt tggatacgta aaattagaac taggatattc agttgtaata     1020
ggagagtttg gaggaaaata tgggcatgga ggcgatccaa gggatgttat atggcaaaat     1080
aagctagttg attggatgat agagaataaa ttttgtgatt tcttttactg gagctggaat     1140
ccagatagtg gagataccgg agggattcta caggatgatt ggacaacaat atgggaagat     1200
aagtataata acctgaagag attgatggat agttgttcca aaagttcttc aagtactcaa     1260
tccgttattc ggagtaccac ccctacaaag tcaaatacaa gtaagaagat ttgtggacca     1320
gcaattctta tcatcctagc agtattctct cttctcttaa gaagggctcc caggtag        1377
```

<210> SEQ ID NO 4
<211> LENGTH: 1377
<212> TYPE: DNA
<213> ORGANISM: Pyrococcus horikoshii EGPh W273A

<400> SEQUENCE: 4

```
atggagggga atactattct taaaatcgta ctaatttgca ctattttagc aggcctattc       60
gggcaagtcg tgccagtata tgcagaaaat acaacatatc aaacaccgac tggaatttac      120
tacgaagtga gaggagatac gatatacatg attaatgtca ccagtggaga ggaaactccc      180
attcatctct ttggtgtaaa ctggtttggc tttgaaacac ctaatcatgt agtgcacgga      240 cttttggaaga gaaactggga agacatgctt cttcagatca aaagcttagg cttcaatgca      300
ataagacttc ctttctgtac tgagtctgta aaaccaggaa cacaaccaat tggaatagat      360
tacagtaaaa atccagatct tcgtggacta gatagcctac agattatgga aaagatcata      420
aagaaggccg gagatcttgg tatctttgtc ttactcgact atcataggat aggatgcact      480
cacatagaac ccctctggta cacggaagac ttctcagagg aagactttat taacacatgg      540
atagaggttg ccaaaaggtt cggtaagtac tggaacgtaa tagggctga tctaaagaat      600 gagcctcata gtgttacctc acccccagct gcttatacag atggtaccgg ggctacatgg      660
ggtatgggaa accctgcaac cgattggaac ttggcggctg agaggatagg aaaagcgatt      720
ctgaaggttg cccctcattg gttgatattc gtggaggga cacaatttac taatccgaag      780
actgacagta gttacaaatg gggctacaac gcttgggcgg gaggaaatct aatggccgta      840
aaggattatc cagttaactt acctaggaat aagctagtat acagccctca cgtatatggg      900
ccagatgtct ataatcaacc gtactttggt cccgctaagg gttttccgga taatcttcca      960
gatatctggt atcaccactt tggatacgta aaattagaac taggatattc agttgtaata     1020
ggagagtttg gaggaaaata tgggcatgga ggcgatccaa gggatgttat atggcaaaat     1080
aagctagttg attggatgat agagaataaa ttttgtgatt tcttttactg gagctggaat     1140
ccagatagtg gagataccgg agggattcta caggatgatt ggacaacaat atgggaagat     1200
aagtataata acctgaagag attgatggat agttgttcca aaagttcttc aagtactcaa     1260
tccgttattc ggagtaccac ccctacaaag tcaaatacaa gtaagaagat ttgtggacca     1320
gcaattctta tcatcctagc agtattctct cttctcttaa gaagggctcc caggtag        1377
```

-continued

<210> SEQ ID NO 5
<211> LENGTH: 33
<212> TYPE: DNA
<213> ORGANISM: Artificial
<220> FEATURE:
<223> OTHER INFORMATION: Primer

<400> SEQUENCE: 5
ggctacaacg cttgggcggg aggaaatcta atg    33

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
cattagattt cctcccgccc aagcgttgta gcc    33

<210> SEQ ID NO 7
<211> LENGTH: 369
<212> TYPE: PRT
<213> ORGANISM: Ignisphaera aggregans EGIa1

<400> SEQUENCE: 7

Met Asn Phe Phe Val Lys Asn Gly Glu Ile Tyr Lys Leu Asp Gly Ala
1               5                   10                  15

Thr Gly Lys Pro Lys Ile Ile Tyr Leu Phe Gly Val Asn Trp Phe Gly
            20                  25                  30

Phe Glu Thr Arg Asp Tyr Val Val His Gly Leu Trp Ala Arg Asn Trp
        35                  40                  45

Val Asp Met Leu Gln Gln Ile Lys Ser Leu Gly Phe Asn Ala Ile Arg
    50                  55                  60

Leu Pro Phe Cys Thr Tyr Ser Val Gln Glu Gly Thr Met Pro Asn Ser
65                  70                  75                  80

Asn Ala Ile Asn Tyr Asn Ile Asn Pro Asp Leu Gln Gly Leu Thr Ser
                85                  90                  95

Ile Glu Ile Met Glu Lys Ile Val Ala Lys Ala Asn Glu Leu Gly Ile
            100                 105                 110

Tyr Ile Leu Leu Asp Tyr His Arg Leu Gly Cys Asp Gln Ile Glu Pro
        115                 120                 125

Leu Trp Tyr Ser Asp Gln Val Ser Glu Gln Gln Phe Ile Asp Thr Trp
    130                 135                 140

Val Ser Val Ala Lys Arg Phe Ala Lys Tyr Pro Asn Val Ile Gly Ala
145                 150                 155                 160

Asp Ile Arg Asn Glu Pro Trp Gly Ala Thr Trp Gly Thr Asp Asp Pro
                165                 170                 175

Ala Thr Asp Trp Arg Leu Ala Val Glu Lys Val Ala Pro Lys Ile Leu
            180                 185                 190

Glu Val Ala Pro His Trp Leu Ile Phe Val Glu Gly Thr Tyr Lys Thr
        195                 200                 205

Arg Pro Asp Ile Asp Glu Arg Ser Trp Tyr Pro Tyr Tyr Ser Tyr Tyr
    210                 215                 220

Val Phe Trp Gly Glu Asn Leu Arg Ala Val Arg Tyr Tyr Pro Val Arg
225                 230                 235                 240

Leu Pro Tyr Glu Lys Ile Val Tyr Ser Pro His Thr Tyr Gly Pro Asp

```
                        245                 250                 255
Val Phe Arg Gln Pro Tyr Phe Asp Asp Pro Ile Phe Pro Glu Asn Met
                260                 265                 270

Arg Ser Ile Trp Met Glu Arg Phe Gly Tyr Val Lys Thr Glu Leu Gly
            275                 280                 285

Tyr Ala Leu Val Val Gly Glu Phe Gly Gly Arg Tyr Gly His Gly Gly
        290                 295                 300

Asp Pro Arg Asp Ile Ile Trp Gln Ile Lys Phe Val Asp Trp Leu Ile
305                 310                 315                 320

Glu Asn Arg Ile Cys Asn Phe Phe Tyr Trp Ser Trp Asn Ala Asn Ser
                325                 330                 335

Gly Asp Thr Gly Gly Ile Leu Lys Asp Asp Trp Thr Asn Ile Trp Glu
            340                 345                 350

Asp Lys Tyr Gln Asn Leu Lys Arg Leu Met Asp Tyr Cys Ser Ser Ile
        355                 360                 365

Asn

<210> SEQ ID NO 8
<211> LENGTH: 369
<212> TYPE: PRT
<213> ORGANISM: Ignisphaera aggregans EGIa1 W227A

<400> SEQUENCE: 8

Met Asn Phe Phe Val Lys Asn Gly Glu Ile Tyr Lys Leu Asp Gly Ala
1               5                   10                  15

Thr Gly Lys Pro Lys Ile Ile Tyr Leu Phe Gly Val Asn Trp Phe Gly
            20                  25                  30

Phe Glu Thr Arg Asp Tyr Val Val His Gly Leu Trp Ala Arg Asn Trp
        35                  40                  45

Val Asp Met Leu Gln Gln Ile Lys Ser Leu Gly Phe Asn Ala Ile Arg
    50                  55                  60

Leu Pro Phe Cys Thr Tyr Ser Val Gln Glu Gly Thr Met Pro Asn Ser
65                  70                  75                  80

Asn Ala Ile Asn Tyr Asn Ile Asn Pro Asp Leu Gln Gly Leu Thr Ser
                85                  90                  95

Ile Glu Ile Met Glu Lys Ile Val Ala Lys Ala Asn Glu Leu Gly Ile
            100                 105                 110

Tyr Ile Leu Leu Asp Tyr His Arg Leu Gly Cys Asp Gln Ile Glu Pro
        115                 120                 125

Leu Trp Tyr Ser Asp Gln Val Ser Glu Gln Gln Phe Ile Asp Thr Trp
    130                 135                 140

Val Ser Val Ala Lys Arg Phe Ala Lys Tyr Pro Asn Val Ile Gly Ala
145                 150                 155                 160

Asp Ile Arg Asn Glu Pro Trp Gly Ala Thr Trp Gly Thr Asp Asp Pro
                165                 170                 175

Ala Thr Asp Trp Arg Leu Ala Val Glu Lys Val Ala Pro Lys Ile Leu
            180                 185                 190

Glu Val Ala Pro His Trp Leu Ile Phe Val Glu Gly Thr Tyr Lys Thr
        195                 200                 205

Arg Pro Asp Ile Asp Glu Arg Ser Trp Tyr Pro Tyr Tyr Ser Tyr Tyr
    210                 215                 220

Val Phe Ala Gly Glu Asn Leu Arg Ala Val Arg Tyr Tyr Pro Val Arg
225                 230                 235                 240

Leu Pro Tyr Glu Lys Ile Val Tyr Ser Pro His Thr Tyr Gly Pro Asp
```

-continued

```
                245                 250                 255
Val Phe Arg Gln Pro Tyr Phe Asp Asp Pro Ile Phe Pro Glu Asn Met
            260                 265                 270

Arg Ser Ile Trp Met Glu Arg Phe Gly Tyr Val Lys Thr Glu Leu Gly
            275                 280                 285

Tyr Ala Leu Val Val Gly Glu Phe Gly Gly Arg Tyr Gly His Gly Gly
    290                 295                 300

Asp Pro Arg Asp Ile Ile Trp Gln Ile Lys Phe Val Asp Trp Leu Ile
305                 310                 315                 320

Glu Asn Arg Ile Cys Asn Phe Phe Tyr Trp Ser Trp Asn Ala Asn Ser
                325                 330                 335

Gly Asp Thr Gly Gly Ile Leu Lys Asp Asp Trp Thr Asn Ile Trp Glu
            340                 345                 350

Asp Lys Tyr Gln Asn Leu Lys Arg Leu Met Asp Tyr Cys Ser Ser Ile
            355                 360                 365

Asn
```

<210> SEQ ID NO 9
<211> LENGTH: 1110
<212> TYPE: DNA
<213> ORGANISM: Ignisphaera aggregans EGIa1

<400> SEQUENCE: 9

```
atgaatttct tgttaaaaaa tggtgaaata tacaaattag atggagctac tggaaaaccc      60
aagattatat atttatttgg tgttaattgg tttggttttg agacgaggga ctatgttgtt     120
catggtttgt gggctaggaa ttgggttgat atgttgcagc agattaagag tcttgggttt     180
aatgctatta gattgccttt ctgtacatat tctgttcagg aaggtacaat gccaaatagt     240
aatgcgatta actataacat taatccagat cttcaaggtc ttacatctat agagattatg     300
gagaagattg ttgcgaaggc taatgaactt ggtatatata tattgcttga ttatcatagg     360
cttggctgcg atcagataga gcctctgtgg tattctgatc aagtgagtga acagcagttt     420
atagatacat gggtaagtgt tgcaaagaga tttgcaaaat atccaaatgt tataggtgca     480
gatattagaa atgagccatg gggagccaca tggggtacag atgacccagc aacagattgg     540
agactagcag tagagaaagt agctccaaag attcttgagg tagctccaca ctggctaata     600
tttgtagagg ggacatataa aacaagacca gatatagatg aaaggagttg gtatccatat     660
tattcatatt atgtatttgg gggagaaaat cttagggctg ttagatacta cccagttaga     720
ctgccatatg agaaaatagt gtattcacca catacatatg ggccagatgt atttcgtcaa     780
ccatattttg atgaccctat atttccagag aatatgcgta gcatatggat ggagcgattc     840
ggctatgtaa aaactgaatt gggatacgca ttagtagtag gagaatttgg tggaaggtat     900
ggccatggtg gagatccaag ggatattata tggcaaataa aatttgttga ttggttgata     960
gagaatagga tatgtaactt cttctactgg agctggaatg caaatagtgg cgatacaggt    1020
ggtattctaa aggatgactg gacaaatatc tgggaagata ataccaaaaa cctgaagcgg    1080
cttatggact attgtagttc aattaattag                                     1110
```

<210> SEQ ID NO 10
<211> LENGTH: 1110
<212> TYPE: DNA
<213> ORGANISM: Ignisphaera aggregans EGIa1 W227A

<400> SEQUENCE: 10

```
atgaatttct tgttaaaaa tggtgaaata tacaaattag atggagctac tggaaaaccc    60
aagattatat atttatttgg tgttaattgg tttggttttg agacgaggga ctatgttgtt   120
catggtttgt gggctaggaa ttgggttgat atgttgcagc agattaagag tcttgggttt   180
aatgctatta gattgccttt ctgtacatat tctgttcagg aaggtacaat gccaaatagt   240
aatgcgatta actataacat taatccagat cttcaaggtc ttacatctat agagattatg   300
gagaagattg ttgcgaaggc taatgaactt ggtatatata tattgcttga ttatcatagg   360
cttggctgcg atcagataga gcctctgtgg tattctgatc aagtgagtga acagcagttt   420
atagatacat gggtaagtgt tgcaaagaga tttgcaaaat atccaaatgt tataggtgca   480
gatattagaa atgagccatg gggagccaca tggggtacag atgacccagc aacagattgg   540
agactagcag tagagaaagt agctccaaag attcttgagg tagctccaca ctggctaata   600
tttgtagagg ggacatataa aacaagacca gatatagatg aaaggagttg gtatccatat   660
tattcatatt atgtatttgc gggagaaaat cttagggctg ttagatacta cccagttaga   720
ctgccatatg agaaaatagt gtattcacca catacatatg ggccagatgt atttcgtcaa   780
ccatattttg atgaccctat atttccagag aatatgcgta gcatatggat ggagcgattc   840
ggctatgtaa aaactgaatt gggatacgca ttagtagtag gagaatttgg tggaaggtat   900
ggccatggtg gagatccaag ggatattata tggcaaataa aatttgttga ttggttgata   960
gagaatagga tatgtaactt cttctactgg agctggaatc aaatagtggg cgatacaggt  1020
ggtattctaa aggatgactg gacaaatatc tgggaagata ataccaaaaa cctgaagcgg  1080
cttatggact attgtagttc aattaattag                                    1110
```

<210> SEQ ID NO 11
<211> LENGTH: 33
<212> TYPE: DNA
<213> ORGANISM: Artificial
<220> FEATURE:
<223> OTHER INFORMATION: Primer

<400> SEQUENCE: 11

```
tcatattatg tatttgcggg agaaaatctt agg                                 33
```

<210> SEQ ID NO 12
<211> LENGTH: 33
<212> TYPE: DNA
<213> ORGANISM: artificial
<220> FEATURE:
<223> OTHER INFORMATION: primer

<400> SEQUENCE: 12

```
cctaagattt tctcccgcaa atacataata tga                                 33
```

<210> SEQ ID NO 13
<211> LENGTH: 393
<212> TYPE: PRT
<213> ORGANISM: Ignisphaera aggregans EGIa2

<400> SEQUENCE: 13

```
Met Tyr Arg Glu Lys Ser Cys Gly Ser Thr Ile Met Asp Val Tyr Tyr
1               5                   10                  15

Arg Ala Arg Gly Thr Glu Ile Tyr Ile Glu Arg Lys Gly Val Glu Lys
            20                  25                  30

Pro Leu Tyr Ile Phe Gly Ile Asn Trp Ala Gly Phe Glu Trp Arg Gly
        35                  40                  45
```

```
Arg Val Val Gly Gly Leu His Val Arg Asn Trp Val Glu Ile Leu Gln
     50                  55                  60

Gln Ile Lys Ser Leu Gly Phe Asn Ala Ile Arg Ile Pro Phe Cys Ala
 65                  70                  75                  80

Glu Ser Val Lys Pro Gly Val Phe Pro Ala Pro Arg Thr Ile Asn Tyr
                 85                  90                  95

Ala Leu Asn Arg Asp Leu Ile Gly Leu Asp Ser Ile Ser Ile Met Glu
                100                 105                 110

Lys Ile Ile Ala Lys Ala Ala Glu Leu Glu Leu Tyr Ile Leu Leu Cys
            115                 120                 125

Phe His Asn Ile Ser Cys Leu Ile Met Glu Pro Leu Trp Tyr Thr Pro
130                 135                 140

Leu Phe Ser Glu Gln Gln Phe Ile Asp Thr Trp Ile Arg Val Ala Lys
145                 150                 155                 160

Arg Phe Ser Arg Tyr Trp Asn Val Ile Gly Ala Glu Leu Tyr Asn Asn
                165                 170                 175

Pro His Gly Arg Leu Pro Pro Ser Tyr Tyr Glu Ser Gly Glu Cys
                180                 185                 190

Ala Thr Trp Gly Met Gly Asn Pro Lys Thr Asp Trp Asn Leu Ala Ala
            195                 200                 205

Glu Arg Ile Gly Arg Ala Val Leu Glu Val Ala Pro His Trp Leu Ile
210                 215                 220

Ile Val Lys Gly Thr Gln Leu Thr Asn Pro Arg Ser Asp Asn Val Pro
225                 230                 235                 240

Leu Tyr Pro Glu Ala Thr Tyr Trp Gly Glu Asn Leu Arg Ala Val Arg
                245                 250                 255

Asp Tyr Pro Val Asn Leu Pro Arg Asp Lys Leu Val Tyr Gly Val Asp
                260                 265                 270

Ile Tyr Gly Pro Asp Val Tyr Met Pro Tyr Phe Asn Asp Pro Asn
            275                 280                 285

Ile Phe Pro Asp Lys Leu Tyr Leu Ile Trp Asp Gln Asn Trp Gly Tyr
290                 295                 300

Val Lys Lys Glu Leu Gly Tyr Pro Leu Ile Ile Ala Glu Phe Gly Gly
305                 310                 315                 320

Leu Tyr Gly Arg Gly Asp Pro Arg Asp Val Ile Trp His Gln Lys Leu
                325                 330                 335

Val Glu Tyr Met Ile Ser Asn Asn Ile Cys His Trp Phe Tyr Asn Ala
            340                 345                 350

Leu Asn Pro Asp Asn Pro Ser Thr Ala Gly Leu Leu Gly Asn Asp Trp
                355                 360                 365

Arg Thr Val Arg Glu Asp Lys Met Ala Leu Leu Arg Arg Ala Met Asp
370                 375                 380

Tyr Cys Arg Glu Arg Tyr Gly Asn Ile
385                 390

<210> SEQ ID NO 14
<211> LENGTH: 393
<212> TYPE: PRT
<213> ORGANISM: Ignisphaera aggregans EG1a2 W248A

<400> SEQUENCE: 14

Met Tyr Arg Glu Lys Ser Cys Gly Ser Thr Ile Met Asp Val Tyr Tyr
 1               5                  10                  15

Arg Ala Arg Gly Thr Glu Ile Tyr Ile Glu Arg Lys Gly Val Glu Lys
                20                  25                  30
```

```
Pro Leu Tyr Ile Phe Gly Ile Asn Trp Ala Gly Phe Glu Trp Arg Gly
             35                  40                  45

Arg Val Val Gly Gly Leu His Val Arg Asn Trp Val Glu Ile Leu Gln
 50                  55                  60

Gln Ile Lys Ser Leu Gly Phe Asn Ala Ile Arg Ile Pro Phe Cys Ala
 65                  70                  75                  80

Glu Ser Val Lys Pro Gly Val Phe Pro Ala Pro Arg Thr Ile Asn Tyr
                 85                  90                  95

Ala Leu Asn Arg Asp Leu Ile Gly Leu Asp Ser Ile Ser Ile Met Glu
            100                 105                 110

Lys Ile Ile Ala Lys Ala Ala Glu Leu Glu Leu Tyr Ile Leu Leu Cys
            115                 120                 125

Phe His Asn Ile Ser Cys Leu Ile Met Glu Pro Leu Trp Tyr Thr Pro
        130                 135                 140

Leu Phe Ser Glu Gln Gln Phe Ile Asp Thr Trp Ile Arg Val Ala Lys
145                 150                 155                 160

Arg Phe Ser Arg Tyr Trp Asn Val Ile Gly Ala Glu Leu Tyr Asn Asn
                165                 170                 175

Pro His Gly Arg Leu Pro Pro Ser Tyr Tyr Glu Ser Gly Glu Cys
            180                 185                 190

Ala Thr Trp Gly Met Gly Asn Pro Lys Thr Asp Trp Asn Leu Ala Ala
            195                 200                 205

Glu Arg Ile Gly Arg Ala Val Leu Glu Val Ala Pro His Trp Leu Ile
210                 215                 220

Ile Val Lys Gly Thr Gln Leu Thr Asn Pro Arg Ser Asp Asn Val Pro
225                 230                 235                 240

Leu Tyr Pro Glu Ala Thr Tyr Ala Gly Glu Asn Leu Arg Ala Val Arg
                245                 250                 255

Asp Tyr Pro Val Asn Leu Pro Arg Asp Lys Leu Val Tyr Gly Val Asp
            260                 265                 270

Ile Tyr Gly Pro Asp Val Tyr Tyr Met Pro Tyr Phe Asn Asp Pro Asn
            275                 280                 285

Ile Phe Pro Asp Lys Leu Tyr Leu Ile Trp Asp Gln Asn Trp Gly Tyr
        290                 295                 300

Val Lys Lys Glu Leu Gly Tyr Pro Leu Ile Ile Ala Glu Phe Gly Gly
305                 310                 315                 320

Leu Tyr Gly Arg Gly Asp Pro Arg Asp Val Ile Trp His Gln Lys Leu
                325                 330                 335

Val Glu Tyr Met Ile Ser Asn Asn Ile Cys His Trp Phe Tyr Asn Ala
            340                 345                 350

Leu Asn Pro Asp Asn Pro Ser Thr Ala Gly Leu Leu Glu Asn Asp Trp
            355                 360                 365

Arg Thr Val Arg Glu Asp Lys Met Ala Leu Leu Arg Arg Ala Met Asp
370                 375                 380

Tyr Cys Arg Glu Arg Tyr Gly Asn Ile
385                 390

<210> SEQ ID NO 15
<211> LENGTH: 1182
<212> TYPE: DNA
<213> ORGANISM: Ignisphaera aggregans EGIa2

<400> SEQUENCE: 15
atgtatagag aaaaatcctg tgggtcaact ataatggatg tgtactacag ggctagggt        60
```

```
acagagatat atattgagag gaaaggtgtt gaaaaacccc tctatatctt tggaataaat    120
tgggctggtt ttgagtggcg aggaagagtt gttggtggtc tccatgtcag aaactgggta    180
gagattctcc agcagataaa gagccttggt ttcaacgcta ttagaatacc attctgtgca    240
gaatctgtta agccaggtgt ttttcctgct ccaagaacaa ttaactatgc attgaataga    300
gatcttattg ggcttgactc catatctatt atggagaaga taattgctaa agcagctgag    360
ctagagctat acatacttct atgcttccac aacataagct gtctaatcat ggaaccacta    420
tggtatacac ccctatttag cgaacaacag tttatagata catggataag agttgcaaag    480
agatttagta gatattggaa tgttataggt gcagaactat ataataatcc acatgggaga    540
ctcccaccat cttactacta tgaaagtgga gagtgtgcta catggggtat gggcaaccct    600
aagactgatt ggaatcttgc tgcagagaga atagggagag ctgttctaga ggttgctcca    660
cactggctaa taattgtaaa aggtacacag ctaacaaatc ccagatcaga taatgtgcca    720
ctatatcccg aggctaccta ctggggtgag aatctcagag ctgtaagaga ctatcctgtg    780
aatctaccga gggataagct tgtatatggt gtcgatatct atggacctga tgtatattat    840
atgccatatt tcaatgaccc aaatatattt ccagataagc tctatcttat atgggatcag    900
aattggggct atgtaaagaa ggagcttgga tatccactaa ttatagcaga gtttggtgga    960
ctctatggaa ggggtgatcc aagggatgtt atatggcatc aaaaacttgt tgagtatatg   1020
attagcaata atatttgtca ctggttctac aatgctttaa atcctgataa tcctagtaca   1080
gctgggttgc ttgagaatga ttggagaact gttagagagg ataagatggc actgcttagg   1140
agggctatgg attactgtag agagagatat ggcaatatat aa                     1182

<210> SEQ ID NO 16
<211> LENGTH: 1182
<212> TYPE: DNA
<213> ORGANISM: Ignisphaera aggregans EG1a2 W248A

<400> SEQUENCE: 16
atgtatagag aaaaatcctg tgggtcaact ataatggatg tgtactacag ggctaggggt     60
acagagatat atattgagag gaaaggtgtt gaaaaacccc tctatatctt tggaataaat    120
tgggctggtt ttgagtggcg aggaagagtt gttggtggtc tccatgtcag aaactgggta    180
gagattctcc agcagataaa gagccttggt ttcaacgcta ttagaatacc attctgtgca    240
gaatctgtta agccaggtgt ttttcctgct ccaagaacaa ttaactatgc attgaataga    300
gatcttattg ggcttgactc catatctatt atggagaaga taattgctaa agcagctgag    360
ctagagctat acatacttct atgcttccac aacataagct gtctaatcat ggaaccacta    420
tggtatacac ccctatttag cgaacaacag tttatagata catggataag agttgcaaag    480
agatttagta gatattggaa tgttataggt gcagaactat ataataatcc acatgggaga    540
ctcccaccat cttactacta tgaaagtgga gagtgtgcta catggggtat gggcaaccct    600
aagactgatt ggaatcttgc tgcagagaga atagggagag ctgttctaga ggttgctcca    660
cactggctaa taattgtaaa aggtacacag ctaacaaatc ccagatcaga taatgtgcca    720
ctatatcccg aggctaccta cgcgggtgag aatctcagag ctgtaagaga ctatcctgtg    780
aatctaccga gggataagct tgtatatggt gtcgatatct atggacctga tgtatattat    840
atgccatatt tcaatgaccc aaatatattt ccagataagc tctatcttat atgggatcag    900
aattggggct atgtaaagaa ggagcttgga tatccactaa ttatagcaga gtttggtgga    960
```

-continued

```
ctctatggaa ggggtgatcc aagggatgtt atatggcatc aaaaacttgt tgagtatatg    1020
attagcaata atatttgtca ctggttctac aatgctttaa atcctgataa tcctagtaca    1080
gctgggttgc ttgagaatga ttggagaact gttagagagg ataagatggc actgcttagg    1140
agggctatgg attactgtag agagagatat ggcaatatat aa                      1182
```

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17

```
cccgaggcta cctacgcggg tgagaatctc aga                                  33
```

<210> SEQ ID NO 18
<211> LENGTH: 33
<212> TYPE: DNA
<213> ORGANISM: Artificial
<220> FEATURE:
<223> OTHER INFORMATION: Primer

<400> SEQUENCE: 18

```
tctgagattc tcacccgcgt aggtagcctc ggg                                  33
```

<210> SEQ ID NO 19
<211> LENGTH: 453
<212> TYPE: PRT
<213> ORGANISM: Staphylothermus hellenicus EGSh

<400> SEQUENCE: 19

```
Met Pro Ala Arg Thr Arg Ile Ala Cys Ala Val Ile Leu Leu Val
1               5                   10                  15

Phe Leu Ala Leu Tyr Ile Ala Trp Pro Val Glu Gly Ser Phe Leu Lys
                20                  25                  30

Gln Gln Pro Tyr Asn Glu Leu Arg Gly Arg Val Leu Gly Ser Asn Ile
        35                  40                  45

Gln Ile Pro Lys Asp His Ile Pro Tyr Tyr His Ile Val Asn Gly Thr
    50                  55                  60

Ile Tyr Met Asp Asp Lys Leu Ile His Leu Phe Gly Val Ser Trp Phe
65                  70                  75                  80

Gly Phe Glu Leu Pro Asp His Ile Val Tyr Gly Leu Trp Ala Arg Asn
                85                  90                  95

Trp Lys Asp Ile Leu Lys Asp Ile Lys Glu Met Gly Phe Asn Ala Ile
                100                 105                 110

Arg Leu Pro Phe Cys His Glu Ser Ile Thr Pro Gly Thr Lys Pro Val
            115                 120                 125

Pro Gly Arg Ile Ser Tyr Ser Leu Asn Pro Asp Leu Arg Asn Leu Thr
        130                 135                 140

Ser Leu Glu Ile Met Glu Lys Ile Ser Tyr Ala Asn Glu Leu Asn
145                 150                 155                 160

Ile Phe Val Leu Leu Asp Tyr His Arg Ile Gly Cys Arg Tyr Ile Glu
                165                 170                 175

Pro Leu Trp Tyr Thr Asp Asn Phe Ser Glu Glu Gln Tyr Ile Lys Asp
            180                 185                 190

Trp Val Phe Leu Ala Gln Lys Phe Gly Lys Tyr Pro Asn Val Ile Gly
        195                 200                 205
```

```
Ala Asp Ile Lys Asn Glu Pro His Asp Ser Ala Ser Trp Gly Thr Gly
    210                 215                 220
Asp Asn Lys Thr Asp Phe Arg Leu Phe Ala Glu Arg Val Gly Gln Ala
225                 230                 235                 240
Ile Leu Gln Val Ala Pro His Trp Leu Ile Phe Ile Glu Gly Val Gln
                245                 250                 255
Tyr Thr His Val Pro Glu Ile Asp Gly Arg Asn Pro Tyr Ser Cys Phe
                260                 265                 270
Trp Gly Glu Asn Leu Met Gly Val Lys Asp Tyr Pro Val Arg Leu Pro
            275                 280                 285
Lys Asp Lys Ile Val Tyr Ser Pro His Val Tyr Gly Pro Ser Val Tyr
290                 295                 300
Asn Met Pro Tyr Phe Asn Asp Pro Glu Phe Pro Arg Asn Leu Pro Lys
305                 310                 315                 320
Ile Trp Glu Leu His Phe Gly Tyr Leu Lys Glu Leu Gly Tyr Ala Ile
                325                 330                 335
Val Ile Gly Glu Trp Gly Gly Arg Tyr Val Gly Lys Asp Lys Val Trp
                340                 345                 350
Gln Asp Ala Phe Ala Asp Trp Leu Ile Gln Lys Gly Ile Tyr Asp Phe
            355                 360                 365
Phe Tyr Trp Cys Leu Asn Pro Glu Ser Gly Asp Thr Gly Gly Ile Phe
    370                 375                 380
Lys Ser Asp Trp Arg Thr Val Asn Gln Asp Lys Leu Asn Leu Ile His
385                 390                 395                 400
Arg Ile Ile Asn Ala Ala Ser Gln Ala Gln Ala Ser Thr Ile Ser Gly
                405                 410                 415
Lys His Asp Trp Lys Thr Tyr Leu Val Leu Ile Ala Pro Thr Leu Leu
            420                 425                 430
Pro Val Leu Ile Leu Val Ile Leu Val Leu Ile Ile Lys Arg Arg
    435                 440                 445
Tyr Thr Lys Lys Gln
    450

<210> SEQ ID NO 20
<211> LENGTH: 453
<212> TYPE: PRT
<213> ORGANISM: Staphylothermus hellenicus EGSh W273A

<400> SEQUENCE: 20

Met Pro Ala Arg Thr Arg Ile Ala Cys Ala Val Ile Leu Leu Leu Val
1               5                   10                  15
Phe Leu Ala Leu Tyr Ile Ala Trp Pro Val Glu Gly Ser Phe Leu Lys
                20                  25                  30
Gln Gln Pro Tyr Asn Glu Leu Arg Gly Arg Val Leu Gly Ser Asn Ile
            35                  40                  45
Gln Ile Pro Lys Asp His Ile Pro Tyr Tyr His Ile Val Asn Gly Thr
        50                  55                  60
Ile Tyr Met Asp Asp Lys Leu Ile His Leu Phe Gly Val Ser Trp Phe
65                  70                  75                  80
Gly Phe Glu Leu Pro Asp His Ile Val Tyr Gly Leu Trp Ala Arg Asn
                85                  90                  95
Trp Lys Asp Ile Leu Lys Asp Ile Lys Glu Met Gly Phe Asn Ala Ile
            100                 105                 110
Arg Leu Pro Phe Cys His Glu Ser Ile Thr Pro Gly Thr Lys Pro Val
        115                 120                 125
```

Pro Gly Arg Ile Ser Tyr Ser Leu Asn Pro Asp Leu Arg Asn Leu Thr
    130                 135                 140

Ser Leu Glu Ile Met Glu Lys Ile Ile Ser Tyr Ala Asn Glu Leu Asn
145                 150                 155                 160

Ile Phe Val Leu Leu Asp Tyr His Arg Ile Gly Cys Arg Tyr Ile Glu
                165                 170                 175

Pro Leu Trp Tyr Thr Asp Asn Phe Ser Glu Glu Gln Tyr Ile Lys Asp
            180                 185                 190

Trp Val Phe Leu Ala Gln Lys Phe Gly Lys Tyr Pro Asn Val Ile Gly
        195                 200                 205

Ala Asp Ile Lys Asn Glu Pro His Asp Ser Ala Ser Trp Gly Thr Gly
    210                 215                 220

Asp Asn Lys Thr Asp Phe Arg Leu Phe Ala Glu Arg Val Gly Gln Ala
225                 230                 235                 240

Ile Leu Gln Val Ala Pro His Trp Leu Ile Phe Ile Glu Gly Val Gln
                245                 250                 255

Tyr Thr His Val Pro Glu Ile Asp Gly Arg Asn Pro Tyr Ser Cys Phe
            260                 265                 270

Ala Gly Glu Asn Leu Met Gly Val Lys Asp Tyr Pro Val Arg Leu Pro
        275                 280                 285

Lys Asp Lys Ile Val Tyr Ser Pro His Val Tyr Gly Pro Ser Val Tyr
290                 295                 300

Asn Met Pro Tyr Phe Asn Asp Pro Glu Phe Pro Arg Asn Leu Pro Lys
305                 310                 315                 320

Ile Trp Glu Leu His Phe Gly Tyr Leu Lys Glu Leu Gly Tyr Ala Ile
                325                 330                 335

Val Ile Gly Glu Trp Gly Gly Arg Tyr Val Gly Lys Asp Lys Val Trp
            340                 345                 350

Gln Asp Ala Phe Ala Asp Trp Leu Ile Gln Lys Gly Ile Tyr Asp Phe
        355                 360                 365

Phe Tyr Trp Cys Leu Asn Pro Glu Ser Gly Asp Thr Gly Gly Ile Phe
370                 375                 380

Lys Ser Asp Trp Arg Thr Val Asn Gln Asp Lys Leu Asn Leu Ile His
385                 390                 395                 400

Arg Ile Ile Asn Ala Ala Ser Gln Ala Gln Ala Ser Thr Ile Ser Gly
                405                 410                 415

Lys His Asp Trp Lys Thr Tyr Leu Val Leu Ile Ala Pro Thr Leu Leu
            420                 425                 430

Pro Val Leu Ile Leu Val Ile Leu Val Leu Leu Ile Ile Lys Arg Arg
        435                 440                 445

Tyr Thr Lys Lys Gln
    450

<210> SEQ ID NO 21
<211> LENGTH: 1362
<212> TYPE: DNA
<213> ORGANISM: Staphylothermus hellenicus EGSh

<400> SEQUENCE: 21
atgccggcta gaactagaat cgcctgcgct gttatcctcc tattagtttt tctagcttta      60
tatatcgcat ggccagtaga gggatcgttt ttgaagcagc aaccctataa tgagcttcga     120
ggccgggttc taggctccaa tatccagatc cccaaagatc acatcccta ctaccacatc      180 gttaatggga ctatctacat ggatgataaa ctaatacatc tctttggagt atcctggttc     240

```
gggttcgagc tcccagatca catagtctac ggtttatggg ctcgtaactg aaggatata      300 ctaaaagaca ttaaggaaat gggttttaac gctataaggc ttcccttctg ccacgaatcc     360 ataaccccg gcactaagcc tgttcctggg aggataagtt atagcttaaa tcctgatctc      420
agaaatctca catccctaga gataatggag aaaataatat catatgctaa cgagctcaat     480
atattcgtct tactagatta tcataggata ggttgtagat atattgagcc actctggtac     540
accgacaact tctctgagga gcagtatatc aaggactggg tgttcctagc ccaaaaattc     600
ggcaaatatc cgaatgtgat aggtgctgat atcaagaatg aaccacatga ctcagcctca     660
tgggggacag gtgataacaa gactgatttt aggctcttcg ctgagagggt gggacaagca     720
atactccaag tagcacctca ctggcttata tttatcgaag gagtccaata cacccatgtc     780
cccgagatcg acgggagaaa cccttattcc tgcttctggg gagaaaactt aatgggtgta     840
aaggattatc cagtaagact tcccaaggat aaaatagtct actccccca cgtctacggt      900 cccagcgtat ataatatgcc ttacttcaac gacccagaat ttcccagaaa cctcccaaag     960
atatgggaac tacacttcgg atacctcaag gaactaggct atgctatagt tataggtgag     1020
tggggaggca gatatgtagg gaaggataag gtgtggcaag acgccttcgc ggactggctc     1080
atccagaaag gcatatatga tttcttctac tggtgcttaa accctgaaag cggtgataca     1140
ggtgggatat tcaaatctga ctggagaaca gttaaccaag ataagctaaa cctaatacat     1200
aggataataa atgctgcaag ccaggcacaa gccagtacaa tatctgggaa acatgactgg     1260
aaaacctacc tggtactcat agctccaaca ctcctacccg tactcatact agtaatacta     1320
gtcctactga tcattaaaag aagatacacc aagaagcaat aa                        1362

<210> SEQ ID NO 22
<211> LENGTH: 1362
<212> TYPE: DNA
<213> ORGANISM: Staphylothermus hellenicus EGSh W273A

<400> SEQUENCE: 22
atgccggcta gaactagaat cgcctgcgct gttatcctcc tattagtttt tctagcttta     60
tatatcgcat ggccagtaga gggatcgttt ttgaagcagc aaccctataa tgagcttcga     120
ggccgggttc taggctccaa tatccagatc cccaaagatc acatccccta ctaccacatc     180
gttaatggga ctatctacat ggatgataaa ctaatacatc tctttggagt atcctggttc     240
gggttcgagc tcccagatca catagtctac ggtttatggg ctcgtaactg aaggatata      300 ctaaaagaca ttaaggaaat gggttttaac gctataaggc ttcccttctg ccacgaatcc     360 ataaccccg gcactaagcc tgttcctggg aggataagtt atagcttaaa tcctgatctc      420
agaaatctca catccctaga gataatggag aaaataatat catatgctaa cgagctcaat     480
atattcgtct tactagatta tcataggata ggttgtagat atattgagcc actctggtac     540
accgacaact tctctgagga gcagtatatc aaggactggg tgttcctagc ccaaaaattc     600
ggcaaatatc cgaatgtgat aggtgctgat atcaagaatg aaccacatga ctcagcctca     660
tgggggacag gtgataacaa gactgatttt aggctcttcg ctgagagggt gggacaagca     720
atactccaag tagcacctca ctggcttata tttatcgaag gagtccaata cacccatgtc     780
cccgagatcg acgggagaaa cccttattcc tgcttcgcgg gagaaaactt aatgggtgta     840
aaggattatc cagtaagact tcccaaggat aaaatagtct actccccca cgtctacggt      900 cccagcgtat ataatatgcc ttacttcaac gacccagaat ttcccagaaa cctcccaaag     960
```

```
atatgggaac tacacttcgg atacctcaag gaactaggct atgctatagt tataggtgag   1020
tggggaggca gatatgtagg gaaggataag gtgtggcaag acgccttcgc ggactggctc   1080
atccagaaag gcatatatga tttcttctac tggtgcttaa accctgaaag cggtgataca   1140
ggtgggatat tcaaatctga ctggagaaca gttaaccaag ataagctaaa cctaatacat   1200
aggataataa atgctgcaag ccaggcacaa gccagtacaa tatctgggaa acatgactgg   1260
aaaacctacc tggtactcat agctccaaca ctcctacccg tactcatact agtaatacta   1320
gtcctactga tcattaaaag aagatacacc aagaagcaat aa                     1362

<210> SEQ ID NO 23
<211> LENGTH: 33
<212> TYPE: DNA
<213> ORGANISM: Artificial
<220> FEATURE:
<223> OTHER INFORMATION: Primer

<400> SEQUENCE: 23
ccttattcct gcttcgcggg agaaaactta atg                                33

<210> SEQ ID NO 24
<211> LENGTH: 33
<212> TYPE: DNA
<213> ORGANISM: Artificial
<220> FEATURE:
<223> OTHER INFORMATION: Primer

<400> SEQUENCE: 24
cattaagttt tctcccgcga agcaggaata agg                                33

<210> SEQ ID NO 25
<211> LENGTH: 514
<212> TYPE: PRT
<213> ORGANISM: Pyrococcus abyssi EGPa

<400> SEQUENCE: 25
```

Met Glu Ile Lys Leu Phe Cys Val Phe Ile Val Phe Ile Ile Leu Phe
1               5                   10                  15

Ser Pro Phe Val Ile Ala Leu Ser Tyr Pro Asp Val Asn Tyr Thr Ala
            20                  25                  30

Glu Asn Gly Ile Ile Phe Val Gln Asn Val Thr Thr Gly Glu Lys Lys
        35                  40                  45

Pro Leu Tyr Leu His Gly Val Ser Trp Phe Gly Phe Glu Leu Lys Asp
    50                  55                  60

His Val Val Tyr Gly Leu Asp Lys Arg Asn Trp Lys Asp Ile Leu Lys
65                  70                  75                  80

Asp Val Lys Arg Leu Gly Phe Asn Ala Ile Arg Leu Pro Phe Cys Ser
                85                  90                  95

Glu Ser Ile Arg Pro Asp Thr Arg Pro Ser Pro Glu Arg Ile Asn Tyr
            100                 105                 110

Glu Leu Asn Pro Asp Leu Lys Asn Leu Thr Ser Leu Glu Ile Met Glu
        115                 120                 125

Lys Ile Ile Glu Tyr Ala Asn Ser Ile Gly Leu Tyr Ile Leu Leu Asp
    130                 135                 140

Tyr His Arg Ile Gly Cys Glu Glu Ile Glu Pro Leu Trp Tyr Thr Glu
145                 150                 155                 160

Asn Tyr Ser Glu Glu Gln Tyr Ile Lys Asp Trp Ile Phe Leu Ala Lys
                165                 170                 175

Arg Phe Gly Lys Tyr Pro Asn Val Ile Gly Ala Asp Ile Lys Asn Glu
                180                 185                 190

Pro His Gly Glu Ala Gly Trp Gly Thr Gly Asp Glu Arg Asp Phe Arg
            195                 200                 205

Leu Phe Ala Glu Lys Val Gly Arg Glu Ile Leu Lys Val Ala Pro His
        210                 215                 220

Trp Leu Ile Phe Val Glu Gly Thr Gln Tyr Thr His Val Pro Asn Ile
225                 230                 235                 240

Asp Glu Ile Ile Glu Lys Lys Gly Trp Trp Thr Phe Trp Gly Glu Asn
                245                 250                 255

Leu Met Gly Val Lys Asp Tyr Pro Val Arg Leu Pro Arg Gly Lys Val
            260                 265                 270

Val Tyr Ser Pro His Val Tyr Gly Pro Ser Val Tyr Met Met Asp Tyr
        275                 280                 285

Phe Lys Ser Pro Asp Phe Pro Asn Asn Met Pro Ile Ile Trp Glu Thr
    290                 295                 300

His Phe Gly Tyr Leu Thr Asp Leu Asn Tyr Thr Leu Val Ile Gly Glu
305                 310                 315                 320

Trp Gly Gly Asn Tyr Glu Gly Leu Asp Lys Val Trp Gln Asp Ala Phe
                325                 330                 335

Val Lys Trp Leu Ile Lys Lys Ile Tyr Asn Phe Phe Tyr Trp Cys
            340                 345                 350

Leu Asn Pro Glu Ser Gly Asp Thr Gly Gly Ile Phe Leu Asp Asp Trp
        355                 360                 365

Lys Thr Val Asn Trp Glu Lys Met Arg Val Ile Tyr Arg Leu Ile Lys
370                 375                 380

Ala Ala Asn Pro Glu Phe Glu Glu Pro Leu Tyr Ile Ile Leu Lys Thr
385                 390                 395                 400

Asn Ala Thr Thr Ser Ile Leu Gly Val Gly Glu Arg Ile Arg Ile Tyr
                405                 410                 415

Trp Tyr Thr Asn Gly Lys Val Ile Asp Ser Asn Phe Ala His Ser Ser
            420                 425                 430

Glu Gly Glu Met Asn Ile Thr Val Thr Lys Ser Met Thr Leu Tyr Ile
        435                 440                 445

Ile Val Lys Lys Gly Asn Gln Thr Leu Arg Lys Glu Leu Lys Leu Tyr
    450                 455                 460

Val Ile Gly Gly Asn Tyr Gly Ser Asn Ile Ser Thr Thr Gln Leu Val
465                 470                 475                 480

Thr Pro Lys Lys Gly Gly Glu Arg Ile Ser Thr Ser Leu Lys Leu Ala
                485                 490                 495

Ile Ser Leu Leu Phe Ile Leu Leu Phe Val Trp Tyr Leu Leu Arg Glu
            500                 505                 510

Lys His

<210> SEQ ID NO 26
<211> LENGTH: 514
<212> TYPE: PRT
<213> ORGANISM: Pyrococcus abyssi EGPa W253A

<400> SEQUENCE: 26

Met Glu Ile Lys Leu Phe Cys Val Phe Ile Val Phe Ile Ile Leu Phe
1               5                   10                  15

Ser Pro Phe Val Ile Ala Leu Ser Tyr Pro Asp Val Asn Tyr Thr Ala
            20                  25                  30

```
Glu Asn Gly Ile Ile Phe Val Gln Asn Val Thr Thr Gly Glu Lys Lys
             35                  40                  45

Pro Leu Tyr Leu His Gly Val Ser Trp Phe Gly Phe Glu Leu Lys Asp
 50                  55                  60

His Val Tyr Gly Leu Asp Lys Arg Asn Trp Lys Asp Ile Leu Lys
 65                  70                  75                  80

Asp Val Lys Arg Leu Gly Phe Asn Ala Ile Arg Leu Pro Phe Cys Ser
                 85                  90                  95

Glu Ser Ile Arg Pro Asp Thr Arg Pro Ser Pro Glu Arg Ile Asn Tyr
                100                 105                 110

Glu Leu Asn Pro Asp Leu Lys Asn Leu Thr Ser Leu Glu Ile Met Glu
            115                 120                 125

Lys Ile Ile Glu Tyr Ala Asn Ser Ile Gly Leu Tyr Ile Leu Leu Asp
130                 135                 140

Tyr His Arg Ile Gly Cys Glu Glu Ile Glu Pro Leu Trp Tyr Thr Glu
145                 150                 155                 160

Asn Tyr Ser Glu Glu Gln Tyr Ile Lys Asp Trp Ile Phe Leu Ala Lys
                165                 170                 175

Arg Phe Gly Lys Tyr Pro Asn Val Ile Gly Ala Asp Ile Lys Asn Glu
            180                 185                 190

Pro His Gly Glu Ala Gly Trp Gly Thr Gly Asp Glu Arg Asp Phe Arg
        195                 200                 205

Leu Phe Ala Glu Lys Val Gly Arg Glu Ile Leu Lys Val Ala Pro His
    210                 215                 220

Trp Leu Ile Phe Val Glu Gly Thr Gln Tyr Thr His Val Pro Asn Ile
225                 230                 235                 240

Asp Glu Ile Ile Glu Lys Lys Gly Trp Trp Thr Phe Ala Gly Glu Asn
                245                 250                 255

Leu Met Gly Val Lys Asp Tyr Pro Val Arg Leu Pro Arg Gly Lys Val
            260                 265                 270

Val Tyr Ser Pro His Val Tyr Gly Pro Ser Val Tyr Met Met Asp Tyr
        275                 280                 285

Phe Lys Ser Pro Asp Phe Pro Asn Asn Met Pro Ile Ile Trp Glu Thr
    290                 295                 300

His Phe Gly Tyr Leu Thr Asp Leu Asn Tyr Thr Leu Val Ile Gly Glu
305                 310                 315                 320

Trp Gly Gly Asn Tyr Glu Gly Leu Asp Lys Val Trp Gln Asp Ala Phe
                325                 330                 335

Val Lys Trp Leu Ile Lys Lys Ile Tyr Asn Phe Phe Tyr Trp Cys
            340                 345                 350

Leu Asn Pro Glu Ser Gly Asp Thr Gly Gly Ile Phe Leu Asp Asp Trp
        355                 360                 365

Lys Thr Val Asn Trp Glu Lys Met Arg Val Ile Tyr Arg Leu Ile Lys
    370                 375                 380

Ala Ala Asn Pro Glu Phe Glu Glu Pro Leu Tyr Ile Ile Leu Lys Thr
385                 390                 395                 400

Asn Ala Thr Thr Ser Ile Leu Gly Val Gly Glu Arg Ile Arg Ile Tyr
                405                 410                 415

Trp Tyr Thr Asn Gly Lys Val Ile Asp Ser Asn Phe Ala His Ser Ser
            420                 425                 430

Glu Gly Glu Met Asn Ile Thr Val Thr Lys Ser Met Thr Leu Tyr Ile
        435                 440                 445

Ile Val Lys Lys Gly Asn Gln Thr Leu Arg Lys Glu Leu Lys Leu Tyr
```

Val Ile Gly Gly Asn Tyr Gly Ser Asn Ile Ser Thr Thr Gln Leu Val
465                 470                 475                 480

Thr Pro Lys Lys Gly Gly Glu Arg Ile Ser Thr Ser Leu Lys Leu Ala
                485                 490                 495

Ile Ser Leu Leu Phe Ile Leu Leu Phe Val Trp Tyr Leu Leu Arg Glu
            500                 505                 510

Lys His

<210> SEQ ID NO 27
<211> LENGTH: 1545
<212> TYPE: DNA
<213> ORGANISM: Pyrococcus abyssi EGPa

<400> SEQUENCE: 27

```
atggagataa aattattttg tgtcttcatt gttttattta tccttttctc gccgtttgtt      60
attgcactaa gttatccaga gtaaaattac actgctgaga atggaattat ctttgtccaa     120
aacgttacaa cggggggaaaa gaagccgctg taccttcacg gtgttagctg gttcggattc     180
gaattgaagg accacgtagt ttatggactc gataaaagaa actggaagga catacttaaa     240
gacgtaaaaa ggctaggttt taatgccatt cgtttaccat tttgcagcga atctataaga     300
cccgatacaa ggccctctcc tgagagaatt aattatgagc tgaatccaga tctaaagaac     360
ttaacttctc tcgagatcat ggagaaaata atagagtacg caaacagtat tggactttac     420
atcctccttg actatcacag gataggatgc gaggaaattg aaccttgtgt gtacactgaa     480
aattacagtg aagagcagta cattaaagat tggatatttc tcgccaagag atttgggaag     540
tacccaaacg tcataggggc tgacataaag aatgaaccac atggtgaagc aggttggggg     600
actggagatg agagagactt tagactttt gctgaaaagg ttggaagaga gatactcaag     660
gttgcccctc attggttaat ctttgttgaa ggaactcaat atacccatgt gcccaatata     720
gatgagataa tagaaaagaa aggatggtgg actttctggg gagagaactt aatgggagta     780
aaggactatc cagttagatt gcctagagga aaagttgtat actcccctca cgtttacgga     840
cctagcgttt atatgatgga ttactttaag agtccagact tcccaaataa catgcctatt     900
atctgggaaa cgcattttgg ttatctcacg gatttaaatt ataccttggt tatcggggag     960
tggggaggaa attatgaggg cttagacaaa gtatggcaag atgctttcgt taatggttta    1020
ataagaaga agatttacaa tttcttctat tggtgtttaa acccggagag tggcgatact    1080
ggcggtatat ttcttgatga ctggaaaact gtaaactggg agaaaatgag agttatctat    1140
cgtctaataa agccgctaa tccagaattt gaggaaccac tatacataat cttaaagacg    1200
aatgctacca catcaatcct gggggttggt gagaggatta ggattattg gtacaccaat    1260
ggtaaagtca ttgattcaaa ctttgctcat agtagtgagg gagagatgaa catcacagtt    1320
acgaagagca tgaccctcta cattattgta aagaaaggaa atcagactct agaaaaggag    1380
ctaaaactgt acgttatagg aggtaattat ggaagtaaca tctcaacaac acaattggta    1440
actcccaaaa aaggaggtga aaggataagt acttcactta gcttgcaat ttccctgctt    1500
ttcatcttac tgttcgtttg gtatcttctc agggaaaaac attga                   1545
```

<210> SEQ ID NO 28
<211> LENGTH: 1545
<212> TYPE: DNA
<213> ORGANISM: Pyrococcus abyssi EGPa W253A

<400> SEQUENCE: 28

```
atggagataa aattattttg tgtcttcatt gttttattta tccttttctc gccgtttgtt      60
attgcactaa gttatccaga tgtaaattac actgctgaga atggaattat ctttgtccaa     120
aacgttacaa cggggggaaaa gaagccgctg taccttcacg gtgttagctg gttcggattc    180
gaattgaagg accacgtagt ttatggactc gataaaagaa actggaagga catacttaaa    240
gacgtaaaaa ggctaggttt taatgccatt cgtttaccat tttgcagcga atctataaga    300
cccgatacaa ggccctctcc tgagagaatt aattatgagc tgaatccaga tctaaagaac    360
ttaacttctc tcgagatcat ggagaaaata atagagtacg caaacagtat tggactttac    420
atcctccttg actatcacag gataggatgc gaggaaattg aacctttgtg gtacactgaa    480
aattacagtg aagagcagta cattaaagat tggatatttc tcgccaagag atttgggaag    540
tacccaaacg tcataggggc tgacataaag aatgaaccac atggtgaagc aggttggggg    600
actggagatg agagagactt tagactttt gctgaaaagg ttggaagaga gatactcaag    660
gttgcccctc attggttaat ctttgttgaa ggaactcaat atacccatgt gcccaatata    720
gatgagataa tagaaaagaa aggatggtgg actttcgcgg gagagaactt aatgggagta    780
aaggactatc cagttagatt gcctagagga aaagttgtat actcccctca cgtttacgga    840
cctagcgttt atatgatgga ttactttaag agtccagact cccaaataa catgcctatt     900
atctgggaaa cgcattttgg ttatctcacg gatttaaatt ataccttggt tatcggggag    960
tggggaggaa attatgaggg cttagacaaa gtatggcaag atgctttcgt taaatggtta   1020
ataaagaaga gatttacaa tttcttctat tggtgtttaa acccggagag tggcgatact    1080
ggcggtatat ttcttgatga ctggaaaact gtaaactggg agaaaatgag agttatctat   1140
cgtctaataa aagccgctaa tccagaattt gaggaaccac tatacataat cttaaagacg   1200
aatgctacca catcaatcct gggggttggt gagaggatta ggattattg gtacaccaat    1260
ggtaaagtca ttgattcaaa cttttgctcat agtagtgagg gagagatgaa catcacagtt   1320
acgaagagca tgaccctcta cattattgta aagaaaggaa atcagactct tagaaaggag   1380
ctaaaactgt acgttatagg aggtaattat ggaagtaaca tctcaacaac acaattggta   1440
actcccaaaa aaggaggtga aaggataagt acttcactta agcttgcaat tccctgctt    1500
ttcatcttac tgttcgtttg gtatcttctc agggaaaaac attga                    1545
```

<210> SEQ ID NO 29
<211> LENGTH: 33
<212> TYPE: DNA
<213> ORGANISM: Artificial
<220> FEATURE:
<223> OTHER INFORMATION: Primer

<400> SEQUENCE: 29

```
ggatggtgga ctttcgcggg agagaactta atg                                   33
```

<210> SEQ ID NO 30
<211> LENGTH: 33
<212> TYPE: DNA
<213> ORGANISM: Artificial
<220> FEATURE:
<223> OTHER INFORMATION: Primer

<400> SEQUENCE: 30

```
cattaagttc tctcccgcga aagtccacca tcc                                   33
```

<210> SEQ ID NO 31
<211> LENGTH: 562
<212> TYPE: PRT
<213> ORGANISM: Acidthermus cellulolyticus EGAc

<400> SEQUENCE: 31

```
Met Pro Arg Ala Leu Arg Arg Val Pro Gly Ser Arg Val Met Leu Arg
1               5                   10                  15

Val Gly Val Val Val Ala Val Leu Ala Leu Val Ala Ala Leu Ala Asn
            20                  25                  30

Leu Ala Val Pro Arg Pro Ala Arg Ala Gly Gly Gly Tyr Trp His
        35                  40                  45

Thr Ser Gly Arg Glu Ile Leu Asp Ala Asn Asn Val Pro Val Arg Ile
50                  55                  60

Ala Gly Ile Asn Trp Phe Gly Phe Glu Thr Cys Asn Tyr Val Val His
65                  70                  75                  80

Gly Leu Trp Ser Arg Asp Tyr Arg Ser Met Leu Asp Gln Ile Lys Ser
                85                  90                  95

Leu Gly Tyr Asn Thr Ile Arg Leu Pro Tyr Ser Asp Asp Ile Leu Lys
            100                 105                 110

Pro Gly Thr Met Pro Asn Ser Ile Asn Phe Tyr Gln Met Asn Gln Asp
        115                 120                 125

Leu Gln Gly Leu Thr Ser Leu Gln Val Met Asp Lys Ile Val Ala Tyr
130                 135                 140

Ala Gly Gln Ile Gly Leu Arg Ile Ile Leu Asp Arg His Arg Pro Asp
145                 150                 155                 160

Cys Ser Gly Gln Ser Ala Leu Trp Tyr Thr Ser Ser Val Ser Glu Ala
                165                 170                 175

Thr Trp Ile Ser Asp Leu Gln Ala Leu Ala Gln Arg Tyr Lys Gly Asn
            180                 185                 190

Pro Thr Val Val Gly Phe Asp Leu His Asn Glu Pro His Asp Pro Ala
        195                 200                 205

Cys Trp Gly Cys Gly Asp Pro Ser Ile Asp Trp Arg Leu Ala Ala Glu
210                 215                 220

Arg Ala Gly Asn Ala Val Leu Ser Val Asn Pro Asn Leu Leu Ile Phe
225                 230                 235                 240

Val Glu Gly Val Gln Ser Tyr Asn Gly Asp Ser Tyr Trp Trp Gly Gly
                245                 250                 255

Asn Leu Gln Gly Ala Gly Gln Tyr Pro Val Val Leu Asn Val Pro Asn
            260                 265                 270

Arg Leu Val Tyr Ser Ala His Asp Tyr Ala Thr Ser Val Tyr Pro Gln
        275                 280                 285

Thr Trp Phe Ser Asp Pro Thr Phe Pro Asn Asn Met Pro Gly Ile Trp
290                 295                 300

Asn Lys Asn Trp Gly Tyr Leu Phe Asn Gln Asn Ile Ala Pro Val Trp
305                 310                 315                 320

Leu Gly Glu Phe Gly Thr Thr Leu Gln Ser Thr Thr Asp Gln Thr Trp
                325                 330                 335

Leu Lys Thr Leu Val Gln Tyr Leu Arg Pro Thr Ala Gln Tyr Gly Ala
            340                 345                 350

Asp Ser Phe Gln Trp Thr Phe Trp Ser Trp Asn Pro Asp Ser Gly Asp
        355                 360                 365

Thr Gly Gly Ile Leu Lys Asp Asp Trp Gln Thr Val Asp Thr Val Lys
370                 375                 380
```

```
Asp Gly Tyr Leu Ala Pro Ile Lys Ser Ser Ile Phe Asp Pro Val Gly
385                 390                 395                 400

Ala Ser Ala Ser Pro Ser Ser Gln Pro Ser Pro Ser Val Ser Pro Ser
            405                 410                 415

Pro Ser Pro Ser Pro Ser Ala Ser Arg Thr Pro Thr Pro Thr Pro Thr
        420                 425                 430

Pro Thr Ala Ser Pro Thr Pro Thr Leu Thr Pro Thr Ala Thr Pro Thr
            435                 440                 445

Pro Thr Ala Ser Pro Thr Pro Ser Pro Thr Ala Ala Ser Gly Ala Arg
        450                 455                 460

Cys Thr Ala Ser Tyr Gln Val Asn Ser Asp Trp Gly Asn Gly Phe Thr
465                 470                 475                 480

Val Thr Val Ala Val Thr Asn Ser Gly Ser Val Ala Thr Lys Thr Trp
            485                 490                 495

Thr Val Ser Trp Thr Phe Gly Gly Asn Gln Thr Ile Thr Asn Ser Trp
        500                 505                 510

Asn Ala Ala Val Thr Gln Asn Gly Gln Ser Val Thr Ala Arg Asn Met
            515                 520                 525

Ser Tyr Asn Asn Val Ile Gln Pro Gly Gln Asn Thr Thr Phe Gly Phe
530                 535                 540

Gln Ala Ser Tyr Thr Gly Ser Asn Ala Ala Pro Thr Val Ala Cys Ala
545                 550                 555                 560

Ala Ser

<210> SEQ ID NO 32
<211> LENGTH: 562
<212> TYPE: PRT
<213> ORGANISM: Acidthermus cellulolyticus EGAc W254A

<400> SEQUENCE: 32

Met Pro Arg Ala Leu Arg Arg Val Pro Gly Ser Arg Val Met Leu Arg
1               5                   10                  15

Val Gly Val Val Val Ala Val Leu Ala Leu Val Ala Ala Leu Ala Asn
            20                  25                  30

Leu Ala Val Pro Arg Pro Ala Arg Ala Ala Gly Gly Gly Tyr Trp His
        35                  40                  45

Thr Ser Gly Arg Glu Ile Leu Asp Ala Asn Asn Val Pro Val Arg Ile
50                  55                  60

Ala Gly Ile Asn Trp Phe Gly Phe Glu Thr Cys Asn Tyr Val Val His
65                  70                  75                  80

Gly Leu Trp Ser Arg Asp Tyr Arg Ser Met Leu Asp Gln Ile Lys Ser
                85                  90                  95

Leu Gly Tyr Asn Thr Ile Arg Leu Pro Tyr Ser Asp Asp Ile Leu Lys
            100                 105                 110

Pro Gly Thr Met Pro Asn Ser Ile Asn Phe Tyr Gln Met Asn Gln Asp
        115                 120                 125

Leu Gln Gly Leu Thr Ser Leu Gln Val Met Asp Lys Ile Val Ala Tyr
130                 135                 140

Ala Gly Gln Ile Gly Leu Arg Ile Ile Leu Asp Arg His Arg Pro Asp
145                 150                 155                 160

Cys Ser Gly Gln Ser Ala Leu Trp Tyr Thr Ser Ser Val Ser Glu Ala
                165                 170                 175

Thr Trp Ile Ser Asp Leu Gln Ala Leu Ala Gln Arg Tyr Lys Gly Asn
            180                 185                 190
```

```
Pro Thr Val Val Gly Phe Asp Leu His Asn Glu Pro His Asp Pro Ala
            195                 200                 205

Cys Trp Gly Cys Gly Asp Pro Ser Ile Asp Trp Arg Leu Ala Ala Glu
210                 215                 220

Arg Ala Gly Asn Ala Val Leu Ser Val Asn Pro Asn Leu Leu Ile Phe
225                 230                 235                 240

Val Glu Gly Val Gln Ser Tyr Asn Gly Asp Ser Tyr Trp Ala Gly Gly
            245                 250                 255

Asn Leu Gln Gly Ala Gly Gln Tyr Pro Val Val Leu Asn Val Pro Asn
            260                 265                 270

Arg Leu Val Tyr Ser Ala His Asp Tyr Ala Thr Ser Val Tyr Pro Gln
            275                 280                 285

Thr Trp Phe Ser Asp Pro Thr Phe Pro Asn Asn Met Pro Gly Ile Trp
290                 295                 300

Asn Lys Asn Trp Gly Tyr Leu Phe Asn Gln Asn Ile Ala Pro Val Trp
305                 310                 315                 320

Leu Gly Glu Phe Gly Thr Thr Leu Gln Ser Thr Thr Asp Gln Thr Trp
            325                 330                 335

Leu Lys Thr Leu Val Gln Tyr Leu Arg Pro Thr Ala Gln Tyr Gly Ala
            340                 345                 350

Asp Ser Phe Gln Trp Thr Phe Trp Ser Trp Asn Pro Asp Ser Gly Asp
            355                 360                 365

Thr Gly Gly Ile Leu Lys Asp Asp Trp Gln Thr Val Asp Thr Val Lys
370                 375                 380

Asp Gly Tyr Leu Ala Pro Ile Lys Ser Ser Ile Phe Asp Pro Val Gly
385                 390                 395                 400

Ala Ser Ala Ser Pro Ser Ser Gln Pro Ser Pro Ser Val Ser Pro Ser
            405                 410                 415

Pro Ser Pro Ser Pro Ser Ala Ser Arg Thr Pro Thr Pro Thr Pro Thr
            420                 425                 430

Pro Thr Ala Ser Pro Thr Pro Thr Leu Thr Pro Thr Ala Thr Pro Thr
            435                 440                 445

Pro Thr Ala Ser Pro Thr Pro Ser Pro Thr Ala Ala Ser Gly Ala Arg
450                 455                 460

Cys Thr Ala Ser Tyr Gln Val Asn Ser Asp Trp Gly Asn Gly Phe Thr
465                 470                 475                 480

Val Thr Val Ala Val Thr Asn Ser Gly Ser Val Ala Thr Lys Thr Trp
            485                 490                 495

Thr Val Ser Trp Thr Phe Gly Gly Asn Gln Thr Ile Thr Asn Ser Trp
            500                 505                 510

Asn Ala Ala Val Thr Gln Asn Gly Gln Ser Val Thr Ala Arg Asn Met
            515                 520                 525

Ser Tyr Asn Asn Val Ile Gln Pro Gly Gln Asn Thr Thr Phe Gly Phe
530                 535                 540

Gln Ala Ser Tyr Thr Gly Ser Asn Ala Ala Pro Thr Val Ala Cys Ala
545                 550                 555                 560

Ala Ser
```

<210> SEQ ID NO 33
<211> LENGTH: 1689
<212> TYPE: DNA
<213> ORGANISM: Acidthermus cellulolyticus EGAc

<400> SEQUENCE: 33

-continued

```
atgccgcgcg cattgcggcg agtgcctggc tcgcgggtga tgctgcgggt cggcgtcgtc    60
gtcgcggtgc tggcattggt tgccgcactc gccaacctag ccgtgccgcg gccggctcgc   120
gccgcgggcg gcggctattg gcacacgagc ggccgggaga tcctggacgc gaacaacgtg   180
ccggtacgga tcgccggcat caactggttt gggttcgaaa cctgcaatta cgtcgtgcac   240
ggtctctggt cacgcgacta ccgcagcatg ctcgaccaga taaagtcgct cggctacaac   300
acaatccggc tgccgtactc tgacgacatt ctcaagccgg gcaccatgcc gaacagcatc   360
aattttttacc agatgaatca ggacctgcag gtctgacgt ccttgcaggt catggacaaa   420
atcgtcgcgt acgccggtca gatcggcctg cgcatcattc ttgaccgcca ccgaccggat   480
tgcagcgggc agtcggcgct gtggtacacg agcagcgtct cggaggctac gtggatttcc   540
gacctgcaag cgctggcgca cgctacaag ggaaacccga cggtcgtcgg ctttgacttg   600
cacaacgagc cgcatgaccc ggcctgctgg ggctgcggcg atccgagcat cgactggcga   660
ttggccgccg agcgggccgg aaacgccgtg ctctcggtga atccgaacct gctcattttc   720
gtcgaaggtg tgcagagcta caacggagac tcctactggt ggggcggcaa cctgcaagga   780
gccggccagt acccggtcgt gctgaacgtg ccgaaccgcc tggtgtactc ggcgcacgac   840
tacgcgacga gcgtctaccc gcagacgtgg ttcagcgatc cgaccttccc caacaacatg   900
cccggcatct ggaacaagaa ctggggatac ctcttcaatc agaacattgc accggtatgg   960
ctgggcgaat cggtacgac actgcaatcc acgaccgacc agacgtggct gaagacgctc  1020
gtccagtacc tacggccgac cgcgcaatac ggtgcggaca gcttccagtg gaccttctgg  1080
tcctggaacc ccgattccgg cgacacagga ggaattctca aggatgactg gcagacggtc  1140
gacacagtaa aagacggcta tctcgcgccg atcaagtcgt cgattttcga tcctgtcggc  1200
gcgtctgcat cgcctagcag tcaaccgtcc ccgtcggtgt cgccgtctcc gtcgccgagc  1260
ccgtcggcga gtcggacgcc gacgcctact ccgacgccga cagccagccc gacgccaacg  1320
ctgaccccta ctgctacgcc cacgcccacg gcaagcccga cgccgtcacc gacggcagcc  1380
tccggagccc gctgcaccgc gagttaccag gtcaacagcg attggggcaa tggcttcacg  1440
gtaacggtgg ccgtgacaaa ttccggatcc gtcgcgacca agacatggac ggtcagttgg  1500
acattcggcg gaaatcagac gattaccaat tcgtggaatg cagcggtcac gcagaacggt  1560
cagtcggtaa cggctcggaa tatgagttat aacaacgtga ttcagcctgg tcagaacacc  1620
acgttcggat tccaggcgag ctataccgga agcaacgcgg caccgacagt cgcctgcgca  1680
gcaagttaa                                                         1689
```

<210> SEQ ID NO 34
<211> LENGTH: 1689
<212> TYPE: DNA
<213> ORGANISM: Acidthermus cellulolyticus EGAc W254A

<400> SEQUENCE: 34

```
atgccgcgcg cattgcggcg agtgcctggc tcgcgggtga tgctgcgggt cggcgtcgtc    60
gtcgcggtgc tggcattggt tgccgcactc gccaacctag ccgtgccgcg gccggctcgc   120
gccgcgggcg gcggctattg gcacacgagc ggccgggaga tcctggacgc gaacaacgtg   180
ccggtacgga tcgccggcat caactggttt gggttcgaaa cctgcaatta cgtcgtgcac   240
ggtctctggt cacgcgacta ccgcagcatg ctcgaccaga taaagtcgct cggctacaac   300
acaatccggc tgccgtactc tgacgacatt ctcaagccgg gcaccatgcc gaacagcatc   360
aattttttacc agatgaatca ggacctgcag gtctgacgt ccttgcaggt catggacaaa   420
```

```
atcgtcgcgt acgccggtca gatcggcctg cgcatcattc ttgaccgcca ccgaccggat    480
tgcagcgggc agtcggcgct gtggtacacg agcagcgtct cggaggctac gtggatttcc    540
gacctgcaag cgctggcgca gcgctacaag ggaaacccga cggtcgtcgg ctttgacttg    600
cacaacgagc gcatgacccc ggcctgctgg ggctgcggcg atccgagcat cgactggcga    660
ttggccgccg agcgggccgg aaacgccgtg ctctcggtga atccgaacct gctcattttc    720
gtcgaaggtg tgcagagcta caacggagac tcctactggg cgggcggcaa cctgcaagga    780
gccggccagt accggtcgt gctgaacgtg ccgaaccgcc tggtgtactc ggcgcacgac    840
tacgcgacga cgtctaccc gcagacgtgg ttcagcgatc cgaccttccc caacaacatg    900
cccggcatct ggaacaagaa ctggggatac ctcttcaatc agaacattgc accggtatgg    960
ctgggcgaat cggtacgac actgcaatcc acgaccgacc agacgtggct gaagacgctc   1020
gtccagtacc tacggccgac cgcgcaatac ggtgcggaca gcttccagtg gaccttctgg   1080
tcctggaacc ccgattccgg cgacacagga ggaattctca aggatgactg gcagacggtc   1140
gacacagtaa aagacggcta tctcgcgccg atcaagtcgt cgattttcga tcctgtcggc   1200
gcgtctgcat cgcctagcag tcaaccgtcc ccgtcggtgt cgccgtctcc gtcgccgagc   1260
ccgtcggcga gtcggacgcc gacgcctact ccgacgccga cagccagccc gacgccaacg   1320
ctgaccccta ctgctacgcc cacgcccacg gcaagcccga cgccgtcacc gacggcagcc   1380
tccggagccc gctgcaccgc gagttaccag gtcaacagcg attggggcaa tggcttcacg   1440
gtaacggtgg ccgtgacaaa ttccggatcc gtcgcgacca agacatggac ggtcagttgg   1500
acattcggcg gaaatcagac gattaccaat tcgtggaatg cagcggtcac gcagaacggt   1560
cagtcggtaa cggctcggaa tatgagttat aacaacgtga ttcagcctgg tcagaacacc   1620
acgttcggat tccaggcgag ctataccgga agcaacgcgg caccgacagt cgcctgcgca   1680
gcaagttaa                                                           1689
```

<210> SEQ ID NO 35
<211> LENGTH: 33
<212> TYPE: DNA
<213> ORGANISM: Artificial
<220> FEATURE:
<223> OTHER INFORMATION: Primer

<400> SEQUENCE: 35
ggagactcct actgggcggg cggcaacctg caa    33

<210> SEQ ID NO 36
<211> LENGTH: 33
<212> TYPE: DNA
<213> ORGANISM: Artificial
<220> FEATURE:
<223> OTHER INFORMATION: Primer

<400> SEQUENCE: 36
ttgcaggttg ccgcccgccc agtaggagtc tcc    33

<210> SEQ ID NO 37
<211> LENGTH: 541
<212> TYPE: PRT
<213> ORGANISM: Spirochaeta thermophila EGSt

<400> SEQUENCE: 37

Met Lys Tyr Leu Arg Thr Ile Leu Leu Ser Leu Leu Val Phe Leu Ile
1               5                   10                  15

```
Thr Leu Gly Cys Ser Leu Pro Phe Leu Asp Val Ser Gly Lys Gly Gly
            20                  25                  30

Thr Ala Ala Arg Ala Thr Glu Leu Arg Val Gly Arg Leu Thr Gly Val
            35                  40                  45

Asn Trp Phe Gly Phe Glu Thr Gly Asn His Val His Gly Leu Trp
 50                  55                  60

Ala Arg Asp Tyr Lys Ser Met Leu Lys Gln Ile Ala Asp Leu Gly Phe
 65                  70                  75                  80

Asn Cys Ile Arg Ile Pro Trp Ala Asn Glu Met Ile Asp Lys Ala Pro
                 85                  90                  95

Asn Ser Ile Gln Ile Asn Pro Ser Gly Val Asp Pro Tyr Thr Gly Glu
                100                 105                 110

Gln Gly Leu Asn Leu Asp Leu Glu Gly Leu Ser Ser Leu Glu Val Leu
            115                 120                 125

Asp Lys Ile Ile Glu Glu Ala Asn Arg Leu Gly Leu Tyr Val Ile Leu
130                 135                 140

Asp Asn His Ser Arg Ala Ala Asp Gly Tyr Met Asn Glu Thr Leu Trp
145                 150                 155                 160

Tyr Thr Asp Glu Tyr Pro Glu Glu Arg Trp Ile Ser Asp Trp Val Met
                165                 170                 175

Met Val Arg Arg Tyr Lys Asn Tyr Pro Asn Val Ile Gly Ala Asp Leu
                180                 185                 190

Asn Asn Glu Pro His Gly Asn Thr Gly Thr Gly Met Lys Pro Pro Ala
            195                 200                 205

Thr Trp Gly Tyr Thr Leu Pro Glu Tyr Gly Asp Thr Asp Trp Lys Ala
            210                 215                 220

Ala Ala Glu Arg Cys Ala Ala Ile Leu Ala Glu Asn Pro Asn Leu
225                 230                 235                 240

Tyr Ile Ile Val Glu Gly Val Glu Glu Tyr Gln Gly Asp Thr Tyr Trp
                245                 250                 255

Trp Gly Gly Asn Leu Lys Gly Val Arg Asp Tyr Pro Ile Thr Ser Ile
            260                 265                 270

Pro Ala Glu Asn Leu Ile Tyr Ser Pro His Glu Tyr Gly Pro Glu Val
            275                 280                 285

Tyr Asn Gln Ser Trp Phe Ser Asp Pro Thr Phe Pro Asp Asn Met Pro
290                 295                 300

Ala Ile Trp Asp Glu His Phe Trp Phe Ile Tyr Lys Glu Asn Ile Ala
305                 310                 315                 320

Pro Val Leu Ile Gly Glu Phe Gly Ile Lys Glu Ala Ser Ala Ala Asp
                325                 330                 335

Pro Ser Ser Val Ala Tyr Gln Trp Phe Thr Thr Phe Met Ala Tyr Val
            340                 345                 350

Gly Asp Lys Ala Ser Trp Thr Phe Trp Ser Trp Asn Pro Asn Ser Gly
            355                 360                 365

Asp Thr Gly Gly Ile Leu Lys Asp Asp Trp Val Thr Val Asn Glu Ala
            370                 375                 380

Lys Tyr Asn Leu Ile Arg Pro Tyr Leu Ala Asn Pro Gln Pro Thr
385                 390                 395                 400

Ala Thr Pro Thr Pro Thr Gly Thr Pro Thr Pro Thr Pro Thr
                405                 410                 415

Pro Thr Pro Thr Pro Thr Pro Thr Pro Thr Pro Thr
            420                 425                 430
```

```
Ala Thr Pro Thr Pro Thr Pro Thr Pro Thr Pro Thr Pro Thr
            435                 440                 445

Pro Thr Ala Thr Pro Thr Pro Ser Gly Glu Tyr Thr Glu Ile Ala Leu
450                 455                 460

Pro Phe Ser Tyr Asp Gly Ala Gly Glu Tyr Tyr Trp Lys Thr Asp Gln
465                 470                 475                 480

Phe Ser Thr Asp Pro Asn Asp Trp Ser Arg Tyr Val Asn Ser Trp Asn
                485                 490                 495

Leu Asp Leu Leu Glu Ile Asn Gly Thr Asp Tyr Thr Asn Val Trp Val
            500                 505                 510

Ala Gln His Gln Ile Pro Ala Ala Ser Asp Gly Tyr Trp Tyr Ile His
        515                 520                 525

Tyr Lys Ser Gly Val Ser Trp Gly His Val Glu Ile Lys
530                 535                 540

<210> SEQ ID NO 38
<211> LENGTH: 541
<212> TYPE: PRT
<213> ORGANISM: Spirochaeta thermophila EGSt W257A

<400> SEQUENCE: 38

Met Lys Tyr Leu Arg Thr Ile Leu Leu Ser Leu Leu Val Phe Leu Ile
1               5                   10                  15

Thr Leu Gly Cys Ser Leu Pro Phe Leu Asp Val Ser Gly Lys Gly Gly
            20                  25                  30

Thr Ala Ala Arg Ala Thr Glu Leu Arg Val Gly Arg Leu Thr Gly Val
        35                  40                  45

Asn Trp Phe Gly Phe Glu Thr Gly Asn His Val Val His Gly Leu Trp
    50                  55                  60

Ala Arg Asp Tyr Lys Ser Met Leu Lys Gln Ile Ala Asp Leu Gly Phe
65                  70                  75                  80

Asn Cys Ile Arg Ile Pro Trp Ala Asn Glu Met Ile Asp Lys Ala Pro
                85                  90                  95

Asn Ser Ile Gln Ile Asn Pro Ser Gly Val Asp Pro Tyr Thr Gly Glu
            100                 105                 110

Gln Gly Leu Asn Leu Asp Leu Glu Gly Leu Ser Ser Leu Glu Val Leu
        115                 120                 125

Asp Lys Ile Ile Glu Glu Ala Asn Arg Leu Gly Leu Tyr Val Ile Leu
130                 135                 140

Asp Asn His Ser Arg Ala Ala Asp Gly Tyr Met Asn Glu Thr Leu Trp
145                 150                 155                 160

Tyr Thr Asp Glu Tyr Pro Glu Glu Arg Trp Ile Ser Asp Trp Val Met
                165                 170                 175

Met Val Arg Arg Tyr Lys Asn Tyr Pro Asn Val Ile Gly Ala Asp Leu
            180                 185                 190

Asn Asn Glu Pro His Gly Asn Thr Gly Thr Gly Met Lys Pro Pro Ala
        195                 200                 205

Thr Trp Gly Tyr Thr Leu Pro Glu Tyr Gly Asp Thr Asp Trp Lys Ala
    210                 215                 220

Ala Ala Glu Arg Cys Ala Ala Ile Leu Ala Glu Asn Pro Asn Leu
225                 230                 235                 240

Tyr Ile Ile Val Glu Gly Val Glu Glu Tyr Gln Gly Asp Thr Tyr Trp
                245                 250                 255

Ala Gly Gly Asn Leu Lys Gly Val Arg Asp Tyr Pro Ile Thr Ser Ile
            260                 265                 270
```

```
Pro Ala Glu Asn Leu Ile Tyr Ser Pro His Glu Tyr Gly Pro Glu Val
            275                 280                 285

Tyr Asn Gln Ser Trp Phe Ser Asp Pro Thr Phe Pro Asp Asn Met Pro
290                 295                 300

Ala Ile Trp Asp Glu His Phe Trp Phe Ile Tyr Lys Glu Asn Ile Ala
305                 310                 315                 320

Pro Val Leu Ile Gly Glu Phe Gly Ile Lys Glu Ala Ser Ala Ala Asp
                325                 330                 335

Pro Ser Ser Val Ala Tyr Gln Trp Phe Thr Thr Phe Met Ala Tyr Val
            340                 345                 350

Gly Asp Lys Ala Ser Trp Thr Phe Trp Ser Trp Asn Pro Asn Ser Gly
            355                 360                 365

Asp Thr Gly Gly Ile Leu Lys Asp Asp Trp Val Thr Val Asn Glu Ala
370                 375                 380

Lys Tyr Asn Leu Ile Arg Pro Tyr Leu Ala Asn Pro Pro Gln Pro Thr
385                 390                 395                 400

Ala Thr Pro Thr Pro Thr Gly Thr Pro Thr Pro Thr Pro Thr Pro Thr
                405                 410                 415

Pro Thr Pro Thr Pro Thr Pro Thr Pro Thr Pro Thr Pro Thr Pro Thr
            420                 425                 430

Ala Thr Pro Thr Pro Thr Pro Thr Pro Thr Pro Thr Pro Thr Pro Thr
            435                 440                 445

Pro Thr Ala Thr Pro Thr Pro Ser Gly Glu Tyr Thr Glu Ile Ala Leu
450                 455                 460

Pro Phe Ser Tyr Asp Gly Ala Gly Glu Tyr Tyr Trp Lys Thr Asp Gln
465                 470                 475                 480

Phe Ser Thr Asp Pro Asn Asp Trp Ser Arg Tyr Val Asn Ser Trp Asn
                485                 490                 495

Leu Asp Leu Leu Glu Ile Asn Gly Thr Asp Tyr Thr Asn Val Trp Val
            500                 505                 510

Ala Gln His Gln Ile Pro Ala Ala Ser Asp Gly Tyr Trp Tyr Ile His
            515                 520                 525

Tyr Lys Ser Gly Val Ser Trp Gly His Val Glu Ile Lys
530                 535                 540

<210> SEQ ID NO 39
<211> LENGTH: 1626
<212> TYPE: DNA
<213> ORGANISM: Spirochaeta thermophila EGSt

<400> SEQUENCE: 39
atgaaatacc tacggacgat ccttcttagc cttttggtgt tcctcatcac gctgggtgt      60 tcgcttccgt tcctcgatgt gtcggggaag ggagggacgg ccgcacgggc tacggagctc    120
cgggtaggga gactcaccgg cgtgaactgg ttcgggttcg agaccggcaa ccatgtggtg    180
cacgggctct gggccaggga ttacaagtcc atgctcaagc agatagcgga tctcgggttc    240
aactgtatca gaatcccgtg ggccaacgag atgatagaca aggcaccgaa cagcattcag    300
attaatccct cgggtgtgga tcctacacc ggggagcagg gactcaacct ggatctcgaa     360
gggctttcct cccttgaggt ccttgacaag atcatagagg aggccaaccg tctcggcctc    420
tacgtgatcc tcgacaacca ctcccgtgcc gctgatggct atatgaacga aaccctctgg    480
tataccgacg agtatcctga ggagaggtgg atctcggact gggtgatgat ggtgcgtcgg    540
tataagaact accccaatgt gatagggggcc gatctcaaca acgagccgca cgggaacact    600
```

```
gggaccggga tgaagccgcc ggctacgtgg ggatacaccc tccccgagta cggcgatacc    660
gactggaagg cagctgccga gcggtgtgct gcggccatcc tcgcggagaa cccgaatctc    720
tacatcatcg tggaagggt agaggagtat cagggcgata cctactggtg gggcggcaat     780
ctcaaaggcg tgagggacta tcccatcacc tccatccctg cggagaacct catctactcc    840
cctcatgagt atggacccga ggtctacaac cagtcctggt tcagcgatcc taccttcct    900 gacaacatgc ctgcgatctg ggatgagcac ttctggttca tctacaagga gaacatcgcc    960
cctgtgctca tagggagtt cggcatcaaa gaggcgtctg cggctgatcc ctcctcggtg   1020
gcctaccagt ggttcacgac cttcatggcc tatgtgggg acaaggcatc gtggacgttt    1080
tggtcctgga atcccaactc tggggataca gggggatcc tcaaggacga ctgggtgacg    1140
gtgaacgagg cgaagtacaa cctcatcagg ccctatctgg ccaatccgcc gcagcctacg    1200
gccacaccca cgcccaccgg cacgccgaca cctactccca cgcccacacc cactcctacg    1260
ccgacgccta ctccaactcc cacaccaact cccacagcga cgcccactcc cacaccgacc    1320
cccactccca cgccgactcc gaccccacc gccactccca caccttccgg ggagtacacc     1380
gagatcgcgc ttcccttcag ctacgatggg gctggtgagt actactggaa gaccgaccag    1440
ttctccacgg atccgaacga ctggagcagg tacgtcaact cgtggaacct ggatctgctg    1500
gagattaacg gacggacta taccaacgtg tgggtggcac aacaccagat ccctgctgcc    1560
tcggacggct actggtacat ccactacaag agcggcgtct cgtggggaca tgtggagata    1620
aagtga                                                               1626

<210> SEQ ID NO 40
<211> LENGTH: 1626
<212> TYPE: DNA
<213> ORGANISM: Spirochaeta thermophila EGSt W257A

<400> SEQUENCE: 40
atgaaatacc tacggacgat ccttcttagc cttttggtgt tcctcatcac gctggggtgt     60
tcgcttccgt tcctcgatgt gtcggggaag ggagggacgg ccgcacgggc tacggagctc    120
cgggtaggga gactcaccgg cgtgaactgg ttcgggttcg agaccggcaa ccatgtggtg    180
cacgggctct gggccaggga ttacaagtcc atgctcaagc agatagcgga tctcgggttc    240
aactgtatca gaatcccgtg ggccaacgag atgatagaca aggcaccgaa cagcattcag    300
attaatccct cgggtgtgga tcctacacc ggggagcagg gactcaacct ggatctcgaa     360
gggctttcct cccttgaggt ccttgacaag atcatagagg aggccaaccg tctcggcctc    420
tacgtgatcc tcgacaacca ctcccgtgcc gctgatggct atatgaacga aaccctctgg    480
tataccgacg agtatcctga ggagaggtgg atctcggact gggtgatgat ggtgcgtcgg    540
tataagaact accccaatgt gatagggggcc gatctcaaca acgagccgca cggaacact    600 gggaccggga tgaagccgcc ggctacgtgg ggatacaccc tccccgagta cggcgatacc    660
gactggaagg cagctgccga gcggtgtgct gcggccatcc tcgcggagaa cccgaatctc    720
tacatcatcg tggaagggt agaggagtat cagggcgata cctactgggc gggcggcaat     780
ctcaaaggcg tgagggacta tcccatcacc tccatccctg cggagaacct catctactcc    840
cctcatgagt atggacccga ggtctacaac cagtcctggt tcagcgatcc taccttcct    900 gacaacatgc ctgcgatctg ggatgagcac ttctggttca tctacaagga gaacatcgcc    960
cctgtgctca tagggagtt cggcatcaaa gaggcgtctg cggctgatcc ctcctcggtg   1020
```

```
gcctaccagt ggttcacgac cttcatggcc tatgtggggg acaaggcatc gtggacgttt    1080
tggtcctgga atcccaactc tggggataca ggggggatcc tcaaggacga ctgggtgacg    1140
gtgaacgagg cgaagtacaa cctcatcagg ccctatctgg ccaatccgcc gcagcctacg    1200
gccacaccca cgcccaccgg cacgccgaca cctactccca cgcccacacc cactcctacg    1260
ccgacgccta ctccaactcc cacaccaact cccacagcga cgcccactcc cacaccgacc    1320
cccactccca cgccgactcc gaccccgacc gccactccca caccttccgg ggagtacacc    1380
gagatcgcgc ttcccttcag ctacgatggg gctggtgagt actactggaa gaccgaccag    1440
ttctccacgg atccgaacga ctggagcagg tacgtcaact cgtggaacct ggatctgctg    1500
gagattaacg ggacggacta taccaacgtg tgggtggcac aacaccagat ccctgctgcc    1560
tcggacggct actggtacat ccactacaag agcggcgtct cgtggggaca tgtggagata    1620
aagtga                                                              1626
```

<210> SEQ ID NO 41
<211> LENGTH: 33
<212> TYPE: DNA
<213> ORGANISM: Artificial
<220> FEATURE:
<223> OTHER INFORMATION: Primer

<400> SEQUENCE: 41
ggcgatacct actgggcggg cggcaatctc aaa                                  33

<210> SEQ ID NO 42
<211> LENGTH: 33
<212> TYPE: DNA
<213> ORGANISM: Artificial
<220> FEATURE:
<223> OTHER INFORMATION: Primer

<400> SEQUENCE: 42
tttgagattg ccgcccgccc agtaggtatc gcc                                  33

<210> SEQ ID NO 43
<211> LENGTH: 33
<212> TYPE: DNA
<213> ORGANISM: Artificial
<220> FEATURE:
<223> OTHER INFORMATION: Primer

<400> SEQUENCE: 43
ggctacaacg cttggtacgg aggaaatcta atg                                  33

<210> SEQ ID NO 44
<211> LENGTH: 33
<212> TYPE: DNA
<213> ORGANISM: Artificial
<220> FEATURE:
<223> OTHER INFORMATION: Primer

<400> SEQUENCE: 44
cattagattt cctccgtacc aagcgttgta gcc                                  33

<210> SEQ ID NO 45
<211> LENGTH: 33
<212> TYPE: DNA
<213> ORGANISM: Artificial
<220> FEATURE:
<223> OTHER INFORMATION: Primer

<400> SEQUENCE: 45

-continued ggctacaacg cttggtttgg aggaaatcta atg                                33

<210> SEQ ID NO 46
<211> LENGTH: 33
<212> TYPE: DNA
<213> ORGANISM: Artificial
<220> FEATURE:
<223> OTHER INFORMATION: Primer

<400> SEQUENCE: 46
cattagattt cctccaaacc aagcgttgta gcc                                33

<210> SEQ ID NO 47
<211> LENGTH: 33
<212> TYPE: DNA
<213> ORGANISM: Artificial
<220> FEATURE:
<223> OTHER INFORMATION: Primer

<400> SEQUENCE: 47
ggctacaacg cttggcatgg aggaaatcta atg                                33

<210> SEQ ID NO 48
<211> LENGTH: 33
<212> TYPE: DNA
<213> ORGANISM: Artificial
<220> FEATURE:
<223> OTHER INFORMATION: Primer

<400> SEQUENCE: 48
cattagattt cctccatgcc aagcgttgta gcc                                33

<210> SEQ ID NO 49
<211> LENGTH: 458
<212> TYPE: PRT
<213> ORGANISM: Pyrococcus horikoshii EGPh W273Y

<400> SEQUENCE: 49

```
Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
    50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175
```

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
            195                 200                 205

Pro Ala Ala Tyr Thr Asp Gly Thr Gly Ala Thr Trp Gly Met Gly Asn
210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Gly Thr Gln Phe
            245                 250                 255

Thr Asn Pro Lys Thr Asp Ser Ser Tyr Lys Trp Gly Tyr Asn Ala Trp
            260                 265                 270

Tyr Gly Gly Asn Leu Met Ala Val Lys Asp Tyr Pro Val Asn Leu Pro
            275                 280                 285

Arg Asn Lys Leu Val Tyr Ser Pro His Val Tyr Gly Pro Asp Val Tyr
            290                 295                 300

Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
            325                 330                 335

Ser Val Val Ile Gly Glu Phe Gly Gly Lys Tyr Gly His Gly Gly Asp
            340                 345                 350

Pro Arg Asp Val Ile Trp Gln Asn Lys Leu Val Asp Trp Met Ile Glu
            355                 360                 365

Asn Lys Phe Cys Asp Phe Phe Tyr Trp Ser Trp Asn Pro Asp Ser Gly
            370                 375                 380

Asp Thr Gly Gly Ile Leu Gln Asp Asp Trp Thr Thr Ile Trp Glu Asp
385                 390                 395                 400

Lys Tyr Asn Asn Leu Lys Arg Leu Met Asp Ser Cys Ser Lys Ser Ser
            405                 410                 415

Ser Ser Thr Gln Ser Val Ile Arg Ser Thr Thr Pro Thr Lys Ser Asn
            420                 425                 430

Thr Ser Lys Lys Ile Cys Gly Pro Ala Ile Leu Ile Ile Leu Ala Val
            435                 440                 445

Phe Ser Leu Leu Leu Arg Arg Ala Pro Arg
450                 455

<210> SEQ ID NO 50
<211> LENGTH: 458
<212> TYPE: PRT
<213> ORGANISM: Pyrococcus horikoshii EGPh W273F

<400> SEQUENCE: 50

Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
            35                  40                  45

Tyr Met Ile Asn Val Thr Ser Gly Glu Glu Thr Pro Ile His Leu Phe
        50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu

```
                  85                  90                  95
Gly Phe Asn Ala Ile Arg Leu Pro Phe Cys Thr Glu Ser Val Lys Pro
                100                 105                 110
Gly Thr Gln Pro Ile Gly Ile Asp Tyr Ser Lys Asn Pro Asp Leu Arg
                115                 120                 125
Gly Leu Asp Ser Leu Gln Ile Met Glu Lys Ile Ile Lys Lys Ala Gly
                130                 135                 140
Asp Leu Gly Ile Phe Val Leu Leu Asp Tyr His Arg Ile Gly Cys Thr
145                 150                 155                 160
His Ile Glu Pro Leu Trp Tyr Thr Asp Phe Ser Glu Glu Asp Phe
                165                 170                 175
Ile Asn Thr Trp Ile Glu Val Ala Lys Arg Phe Gly Lys Tyr Trp Asn
                180                 185                 190
Val Ile Gly Ala Asp Leu Lys Asn Glu Pro His Ser Val Thr Ser Pro
                195                 200                 205
Pro Ala Ala Tyr Thr Asp Gly Thr Gly Ala Thr Trp Gly Met Gly Asn
                210                 215                 220
Pro Ala Thr Asp Trp Asn Leu Ala Ala Glu Arg Ile Gly Lys Ala Ile
225                 230                 235                 240
Leu Lys Val Ala Pro His Trp Leu Ile Phe Val Glu Gly Thr Gln Phe
                245                 250                 255
Thr Asn Pro Lys Thr Asp Ser Ser Tyr Lys Trp Gly Tyr Asn Ala Trp
                260                 265                 270
Phe Gly Gly Asn Leu Met Ala Val Lys Asp Tyr Pro Val Asn Leu Pro
                275                 280                 285
Arg Asn Lys Leu Val Tyr Ser Pro His Val Tyr Gly Pro Asp Val Tyr
                290                 295                 300
Asn Gln Pro Tyr Phe Gly Pro Ala Lys Gly Phe Pro Asn Leu Pro
305                 310                 315                 320
Asp Ile Trp Tyr His His Phe Gly Tyr Val Lys Leu Glu Leu Gly Tyr
                325                 330                 335
Ser Val Val Ile Gly Glu Phe Gly Gly Lys Tyr Gly His Gly Gly Asp
                340                 345                 350
Pro Arg Asp Val Ile Trp Gln Asn Lys Leu Val Asp Trp Met Ile Glu
                355                 360                 365
Asn Lys Phe Cys Asp Phe Phe Tyr Trp Ser Trp Asn Pro Asp Ser Gly
                370                 375                 380
Asp Thr Gly Gly Ile Leu Gln Asp Asp Trp Thr Thr Ile Trp Glu Asp
385                 390                 395                 400
Lys Tyr Asn Asn Leu Lys Arg Leu Met Asp Ser Cys Ser Lys Ser Ser
                405                 410                 415
Ser Ser Thr Gln Ser Val Ile Arg Ser Thr Thr Pro Thr Lys Ser Asn
                420                 425                 430
Thr Ser Lys Lys Ile Cys Gly Pro Ala Ile Leu Ile Leu Ala Val
                435                 440                 445
Phe Ser Leu Leu Leu Arg Arg Ala Pro Arg
450                 455

<210> SEQ ID NO 51
<211> LENGTH: 458
<212> TYPE: PRT
<213> ORGANISM: Pyrococcus horikoshii EGPh W273H

<400> SEQUENCE: 51
```

```
Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Thr Pro Ile His Leu Phe
    50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
            115                 120                 125

Gly Leu Asp Ser Leu Gln Ile Met Glu Lys Ile Ile Lys Lys Ala Gly
        130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205

Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270

His Gly Gly Asn Leu Met Ala Val Lys Asp Tyr Pro Val Asn Leu Pro
        275                 280                 285

Arg Asn Lys Leu Val Tyr Ser Pro His Val Tyr Gly Pro Asp Val Tyr
    290                 295                 300

Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
                325                 330                 335

Ser Val Val Ile Gly Glu Phe Gly Lys Tyr Gly His Gly Gly Asp
            340                 345                 350

Pro Arg Asp Val Ile Trp Gln Asn Lys Leu Val Asp Trp Met Ile Glu
        355                 360                 365

Asn Lys Phe Cys Asp Phe Phe Tyr Trp Ser Trp Asn Pro Asp Ser Gly
    370                 375                 380

Asp Thr Gly Gly Ile Leu Gln Asp Asp Trp Thr Ile Trp Glu Asp
385                 390                 395                 400

Lys Tyr Asn Asn Leu Lys Arg Leu Met Asp Ser Cys Ser Lys Ser Ser
                405                 410                 415

Ser Ser Thr Gln Ser Val Ile Arg Ser Thr Thr Pro Thr Lys Ser Asn
```

```
                420              425              430
Thr Ser Lys Lys Ile Cys Gly Pro Ala Ile Leu Ile Ile Leu Ala Val
        435              440              445

Phe Ser Leu Leu Leu Arg Arg Ala Pro Arg
450              455
```